(12) United States Patent
Messerchmidt

(10) Patent No.: US 9,041,923 B2
(45) Date of Patent: May 26, 2015

(54) PERI-CRITICAL REFLECTION SPECTROSCOPY DEVICES, SYSTEMS, AND METHODS

(75) Inventor: Robert G. Messerchmidt, Los Altos, CA (US)

(73) Assignee: Rare Light, Inc., Mountain View, CA (US)

( * ) Notice: Subject to any disclaimer, the term of this patent is extended or adjusted under 35 U.S.C. 154(b) by 488 days.

(21) Appl. No.: 13/263,386

(22) PCT Filed: Apr. 7, 2010

(86) PCT No.: PCT/US2010/030299
§ 371 (c)(1),
(2), (4) Date: Dec. 28, 2011

(87) PCT Pub. No.: WO2010/118175
PCT Pub. Date: Oct. 14, 2010

(65) Prior Publication Data
US 2012/0088486 A1 Apr. 12, 2012

Related U.S. Application Data

(60) Provisional application No. 61/167,505, filed on Apr. 7, 2009, provisional application No. 61/226,677, filed on Jul. 17, 2009.

(51) Int. Cl.
*G01J 3/44* (2006.01)
*G01N 21/552* (2014.01)
(Continued)

(52) U.S. Cl.
CPC ............... *G01N 21/552* (2013.01); *G01J 3/02* (2013.01); *G01J 3/0205* (2013.01); *G01J 3/0264* (2013.01); *G01J 3/42* (2013.01); *G01J 3/427* (2013.01)

(58) Field of Classification Search
CPC .......... G01J 3/0205; G01J 3/02; G01J 3/42; G01J 3/427; G01J 3/0264; G01N 21/552
USPC .................................... 356/301–334, 445, 73
See application file for complete search history.

(56) References Cited

U.S. PATENT DOCUMENTS 3,645,631 A 2/1972 Gupta
4,692,024 A 9/1987 Bloss
(Continued)

FOREIGN PATENT DOCUMENTS

CN 1629618 A 6/2005
CN 1749735 A 3/2006
(Continued)

OTHER PUBLICATIONS

"International Application Serial No. PCT/US2010/030299, Search Report mailed Jan. 31, 2011", 5 pgs.
(Continued)

*Primary Examiner* — Kara E Geisel
*Assistant Examiner* — Dominic J Bologna
(74) *Attorney, Agent, or Firm* — Schwegman Lundberg & Woessner, P.A.

(57) ABSTRACT

Spectroscopy apparatuses oriented to the critical angle of the sample are described that detecting the spectral characteristics of a sample wherein the apparatus consists of an electromagnetic radiation source adapted to excite a sample with electromagnetic radiation introduced to the sample at a location at an angle of incidence at or near a critical angle of the sample; a transmitting crystal in communication with the electromagnetic radiation source and the sample, the transmitting crystal having a high refractive index adapted to reflect the electromagnetic radiation internally; a reflector adapted to introduce the electromagnetic radiation to the sample at or near an angle of incidence near the critical angle between the transmitting crystal and sample; and a detector for detecting the electromagnetic radiation from the sample. Also, provided herein are methods, systems, and kits incorporating the peri-critical reflection spectroscopy apparatus.

75 Claims, 9 Drawing Sheets

(51) Int. Cl.
  *G01J 3/02* (2006.01)
  *G01J 3/42* (2006.01)
  *G01J 3/427* (2006.01)

(56) References Cited

U.S. PATENT DOCUMENTS

| | | | |
|---|---|---|---|
| 4,730,882 A | 3/1988 | Messerschmidt et al. | |
| 5,206,699 A | 4/1993 | Stewart et al. | |
| 5,229,833 A | 7/1993 | Stewart | |
| 5,251,008 A | 10/1993 | Masutani | |
| 5,296,702 A | 3/1994 | Beck et al. | |
| 5,444,528 A | 8/1995 | Puschell | |
| 5,784,157 A | 7/1998 | Gorfinkel et al. | |
| 5,786,893 A | 7/1998 | Fink et al. | |
| 5,943,122 A | 8/1999 | Holmes | |
| 5,946,083 A | 8/1999 | Melendez et al. | |
| 6,141,100 A * | 10/2000 | Burka et al. | 356/451 |
| 6,362,144 B1 | 3/2002 | Berman et al. | |
| 6,370,406 B1 | 4/2002 | Wach et al. | |
| 6,417,924 B1 | 7/2002 | Kimura | |
| 6,430,424 B1 | 8/2002 | Berman et al. | |
| 6,462,809 B1 | 10/2002 | Ryan et al. | |
| 6,493,080 B1 | 12/2002 | Boese | |
| 6,493,097 B1 | 12/2002 | Ivarsson | |
| 6,690,966 B1 | 2/2004 | Rava et al. | |
| 6,748,250 B1 | 6/2004 | Berman et al. | |
| 6,841,792 B2 | 1/2005 | Bynum et al. | |
| 6,862,094 B2 | 3/2005 | Johansen | |
| 6,906,327 B2 | 6/2005 | Shelley et al. | |
| 6,908,773 B2 | 6/2005 | Il et al. | |
| 6,992,770 B2 | 1/2006 | Naya | |
| 7,046,359 B2 | 5/2006 | Voigt et al. | |
| 7,057,731 B2 | 6/2006 | Naya | |
| 7,081,958 B2 | 7/2006 | Ivarsson | |
| 7,154,599 B2 | 12/2006 | Adams et al. | |
| 7,317,526 B2 | 1/2008 | Voigt et al. | |
| 7,336,355 B2 | 2/2008 | Ishibashi et al. | |
| 7,379,179 B2 | 5/2008 | Nelson et al. | |
| 7,460,236 B2 | 12/2008 | Ivarsson | |
| 7,564,547 B2 | 7/2009 | Yoo | |
| 7,791,729 B2 | 9/2010 | Higashi et al. | |
| 8,101,426 B2 | 1/2012 | Durack et al. | |
| 8,194,247 B2 | 6/2012 | Sun et al. | |
| 8,730,468 B2 | 5/2014 | Messerchmidt | |
| 2002/0097398 A1 | 7/2002 | Parce | |
| 2002/0182743 A1 | 12/2002 | Perkins et al. | |
| 2003/0156278 A1 | 8/2003 | Yilmaz et al. | |
| 2004/0201849 A1 | 10/2004 | Codner et al. | |
| 2005/0214167 A1 | 9/2005 | Archibald et al. | |
| 2005/0229698 A1 | 10/2005 | Beecroft | |
| 2006/0038980 A1 | 2/2006 | Naka et al. | |
| 2006/0043301 A1 | 3/2006 | Mantele et al. | |
| 2006/0134669 A1 | 6/2006 | Casasanta, III | |
| 2006/0164633 A1* | 7/2006 | Koshoubu et al. | 356/300 |
| 2006/0187459 A1 | 8/2006 | Ok et al. | |
| 2007/0013912 A1 | 1/2007 | Ivarsson | |
| 2007/0030489 A1 | 2/2007 | Salamon et al. | |
| 2007/0081163 A1* | 4/2007 | Liang et al. | 356/445 |
| 2007/0098594 A1 | 5/2007 | Elkin et al. | |
| 2010/0110423 A1 | 5/2010 | Villaumie | |
| 2010/0153323 A1 | 6/2010 | Hennessy et al. | |
| 2010/0259254 A1* | 10/2010 | Verschuren et al. | 324/244 |
| 2010/0278697 A1 | 11/2010 | Koo et al. | |
| 2011/0001965 A1 | 1/2011 | Messerchmidt | |
| 2011/0102768 A1 | 5/2011 | Dosmann et al. | |
| 2011/0188030 A1 | 8/2011 | Verschuren et al. | |
| 2012/0019819 A1 | 1/2012 | Messerchmidt | |
| 2014/0252233 A1 | 9/2014 | Messerchmidt | |

FOREIGN PATENT DOCUMENTS

| | | | |
|---|---|---|---|
| CN | 101023331 A | 8/2007 | |
| CN | 101074921 A | 11/2007 | |
| CN | 101149342 A | 3/2008 | |
| CN | 101300478 A | 11/2008 | |
| CN | 101836102 A | 9/2010 | |
| CN | 102369420 A | 3/2012 | |
| EP | 1666871 A2 | 6/2006 | |
| HK | 1167709 A | 7/2012 | |
| IN | 8577DELNP2001 A | 2/2013 | |
| JP | 04282435 A | 10/1992 | |
| JP | 06505183 A | 6/1994 | |
| JP | 06288902 A | 10/1994 | |
| JP | 10115573 A | 5/1998 | |
| JP | 11132941 A | 5/1999 | |
| JP | 1999132941 | 5/1999 | |
| JP | 2000-180353 A | 6/2000 | |
| JP | 2000180353 A | 6/2000 | |
| JP | 2001511249 A | 8/2001 | |
| JP | 2002162346 A | 6/2002 | |
| JP | 2002174591 A | 6/2002 | |
| JP | 3303100 B2 | 7/2002 | |
| JP | 2002530643 A | 9/2002 | |
| JP | 2003046171 A | 2/2003 | |
| JP | 2004500571 A | 1/2004 | |
| JP | 2004-117298 A | 4/2004 | |
| JP | 2004527741 A | 9/2004 | |
| JP | 2005502895 A | 1/2005 | |
| JP | 2005233928 A | 9/2005 | |
| JP | 2005241278 A | 9/2005 | |
| JP | 2005315680 A | 11/2005 | |
| JP | 2006-507504 A | 3/2006 | |
| JP | 2006189741 A | 7/2006 | |
| JP | 2006201163 A | 8/2006 | |
| JP | 2006317349 A | 11/2006 | |
| JP | 2007127670 A | 5/2007 | |
| JP | 2008-070391 A | 3/2008 | |
| JP | 2008-224240 A | 9/2008 | |
| JP | 2009-192544 A | 8/2009 | |
| JP | 2010520471 A | 6/2010 | |
| JP | 2010156556 A | 7/2010 | |
| JP | 2011511292 A | 4/2011 | |
| JP | 2014513799 A | 6/2014 | |
| KR | 100273711 B1 | 3/2001 | |
| KR | 1020040067322 A | 7/2004 | |
| KR | 102006002003 A | 3/2006 | |
| KR | 100628877 B1 | 9/2006 | |
| KR | 100668323 B1 | 1/2007 | |
| KR | 1020070049088 A | 5/2007 | |
| KR | 1020070059404 A | 6/2007 | |
| WO | WO-9802730 A1 | 1/1998 | |
| WO | WO-9834098 A1 | 8/1998 | |
| WO | WO-0029830 A1 | 5/2000 | |
| WO | WO-2005088277 A1 | 9/2005 | |
| WO | WO-2007121406 A2 | 10/2007 | |
| WO | WO-2009137122 A2 | 11/2009 | |
| WO | WO-2009137122 A3 | 11/2009 | |
| WO | WO-2010090842 A2 | 8/2010 | |
| WO | WO-2010118175 A2 | 10/2010 | |
| WO | WO-2010118175 A3 | 10/2010 | |
| WO | WO-2010090842 A3 | 11/2010 | |
| WO | WO-2012149343 A1 | 11/2012 | |

OTHER PUBLICATIONS

"International Application Serial No. PCT/US2010/030299, Written Opinion mailed Jan. 31, 2011", 3 pgs.
"U.S. Appl. No. 12/865,698, Non Final Office Action mailed Mar. 14, 2013", 7 pgs.
"U.S. Appl. No. 12/865,698, Non Final Office Action mailed Jun. 22, 2012", 7 pgs.
"U.S. Appl. No. 12/865,698, Notice of Allowance mailed Sep. 5, 2013", 8 pgs.
"U.S. Appl. No. 12/865,698, Notice of Allowance mailed Oct. 16, 2012", 7 pgs.
"U.S. Appl. No. 12/865,698, Notice of Allowance mailed Dec. 26, 2013", 6 pgs.
"U.S. Appl. No. 12/865,698, Preliminary Amendment filed Jul. 30, 2010", 8 pgs.
"U.S. Appl. No. 12/865,698, Response filed Aug. 14, 2013 to Non Final Office Action mailed Mar. 14, 2013", 10 pgs.
"U.S. Appl. No. 12/865,698, Response filed Sep. 24, 2012 to Non Final Office Action mailed Jun. 22, 2012", 10 pgs.

(56) References Cited

OTHER PUBLICATIONS

"U.S. Appl. No. 14/281,315, Preliminary Amendment filed Jun. 2, 2014", 6 pgs.
"Australian Application Serial No. 2010234465, First Examination Report mailed Aug. 14, 2012", 2 pgs.
"Canadian Application Serial No. 2,758,113, Office Action mailed Dec. 13, 2013", 3 pgs.
"Chinese Application Serial No. 200980112418.9, Decision mailed Mar. 11, 2014", (w/ English Translation), 24 pgs.
"Chinese Application Serial No. 200980112418.9, Office Action mailed Jun. 19, 2013", 10 pgs.
"Chinese Application Serial No. 200980112418.9, Office Action mailed Nov. 28, 2012", 32 pgs.
"Chinese Application Serial No. 200980112418.9, Response filed Feb. 16, 2013 to Office Action mailed Nov. 28, 2012", 12 pgs.
"Chinese Application Serial No. 200980112418.9, Response filed Jul. 19, 2012 to Office Action mailed Jan. 5, 2012", (w/ English Translation of Claims), 11 pgs.
"Chinese Application Serial No. 200980112418.9, Response filed Nov. 4, 2013 to Office Action mailed Jun. 19, 2013", 12 pgs.
"Chinese Application Serial No. 2009801124189, Office Action mailed Jan. 5, 2012", (w/ English Translation), 14 pgs.
"Chinese Application Serial No. 201080025328.9, Office Action mailed Aug. 21, 2013", 10 pgs.
"International Application Serial No. PCT/US2009/032706, International Search Report mailed Nov. 27, 2009", 2 pgs.
"International Application Serial No. PCT/US2010/030299, International Preliminary Report on Patentability mailed Oct. 20, 2011", 5 pgs.
"Japanese Application Serial No. 2010-545225, Office Action mailed Jan. 29, 2014", 7 pgs.
"Japanese Application Serial No. 2010-545225, Office Action mailed Dec. 20, 2012", (w/ English Translation), 6 pgs.
"Japanese Application Serial No. 2012-504837, Office Action mailed Dec. 4, 2013", 4 pgs.
"Korean Application Serial No. 10-2010-7019454, Amended Claims filed Feb. 15, 2013", 9 pgs.
"Korean Application Serial No. 10-2010-7019454, Appeal Brief filed Mar. 19, 2013", 13 pgs.
"Korean Application Serial No. 10-2010-7019454, Notice of Final Rejection mailed Jan. 16, 2013", 3 pgs.
"Korean Application Serial No. 10-2010-7019454, Office Action mailed Jul. 31, 2013", 23 pgs.
"Korean Application Serial No. 10-2011-7026540, Notice of Final Rejection mailed May 21, 2014", 5 pgs.
"Korean Application Serial No. 10-2011-7026540, Notice of Preliminary Rejection mailed Aug. 20, 2013", (w/ English Translation), 11 pgs.
"Korean Application Serial No. 10-2011-7026540, Notice of Preliminary Rejection mailed Nov. 30, 2012", (w/ English Translation), 5 pgs.
"Korean Application Serial No. 10-2011-7026540, Response and Amendment filed Jan. 6, 2014 to Notice of Preliminary Rejection mailed Aug. 20, 2013", (w/ English Translation of Amended Claims), 42 pgs.
"Korean Application Serial No. 10-2013-7006842, Amendment filed Feb. 25, 2014", 12 pgs.
"Korean Application Serial No. 10-2013-7006842, Notice of Preliminary Rejection mailed Apr. 30, 2014", 11 pgs.
"Korean Application Serial No. 2010-7019454, Response filed Sep. 11, 2012 to Office Action mailed May 14, 2012", 21 pgs.
"European Applicaton Serial No. 10762403.3, Supplementary European Search Report mailed Aug. 7, 2014", 6 pgs.
"Japanese Application Serial No. 2012-504837, Office Action mailed Aug. 4, 2014", (w/ English Translation), 4 pgs.
"U.S. Appl. No. 13/098,140, Non Final Office Action mailed Feb. 12, 2014", 13 pgs.
"U.S. Appl. No. 13/098,140, Notice of Allowance mailed Jul. 10, 2014", 11 pgs.
"U.S. Appl. No. 13/098,140, Response filed May 12, 2014 to Non Final Office Aciton mailed Feb. 12, 2014", 12 pgs.
"U.S. Appl. No. 13/145,711, Examiner Interview Summary mailed Apr. 11, 2014", 3 pgs.
"U.S. Appl. No. 13/145,711, Examiner Interview Summary mailed Aug. 14, 2013", 3 pgs.
"U.S. Appl. No. 13/145,711, Final Office Action mailed Nov. 29, 2013", 20 pgs.
"U.S. Appl. No. 13/145,711, Non Final Office Action mailed Jul. 19, 2013", 26 pgs.
"U.S. Appl. No. 13/145,711, Non Final Office Action mailed Jul. 24, 2014", 31 pgs.
"U.S. Appl. No. 13/145,711, Response filed Mar. 31, 2014 to Final Office Action mailed Nov. 29, 2013", 14 pgs.
"U.S. Appl. No. 13/145,711, Response filed Oct. 21, 2013 to Non Final Office Action mailed Jul. 19, 2013", 14 pgs.
"Australian Application Serial No. 2012249441, Amendment filed Sep. 27, 2013", 9 pgs.
"Canadian Application Serial No. 2,758,113, Response filed Jun. 10, 2014 to Office Action mailed Dec. 13, 2013", 38 pgs.
"Canadian Application Serial No. 2,832,045, Office Action mailed Sep. 30, 2014", 2 pgs.
"Canadian Application Serial No. 2,832,045, Voluntary Amendment filed Jan. 7, 2014", 20 pgs.
"Chinese Application Serial No. 200980112418.9, Response filed Jun. 26, 2014 to Decision mailed Mar. 11, 2014", w/English Claims, 7 pgs.
"Chinese Application Serial No. 201080013124.3, Office Action mailed May 28, 2014", w/English Translation, 26 pgs.
"Chinese Application Serial No. 201080013124.3, Office Action mailed May 31, 2013", w/English Translation, 21 pgs.
"Chinese Application Serial No. 201080013124.3, Office Action mailed Dec. 17, 2013", w/English Translation, 25 pgs.
"Chinese Application Serial No. 201080013124.3, Response filed Sep. 12, 2014 to Office Action mailed May 28, 2014", w/English Translation, 21 pgs.
"European Application Serial No. 09743109.2, European Search Report mailed Dec. 19, 2012", 10 pgs.
"European Application Serial No. 09743109.2, Office Action mailed Sep. 8, 2010", 2 pgs.
"European Application Serial No. 09743109.2, Response filed Jul. 17, 2013 to European Search Report mailed Dec. 19, 2012", 12 pgs.
"European Application Serial No. 09743109.2, Response filed Oct. 7, 2010 to Office Action mailed Sep. 8, 2010", 6 pgs.
"European Application Serial No. 10738933.0, Extended European Search Report mailed Jun. 28, 2013", 6 pgs.
"European Application Serial No. 10738933.0, Response filed Jan. 24, 2014 to European Search Report mailed Jun. 28, 2013", 7 pgs.
"European Application Serial No. 10738933.0, Response filed Apr. 17, 2012 to Office Action mailed Oct. 19, 2012", 3 pgs.
"European Application Serial No. 12722961.5, Office Action mailed Jan. 9, 2014", 2 pgs.
"International Application Serial No. PCT/US2009/032706, International Preliminary Report on Patentability mailed Aug. 12, 2010", 6 pgs.
"International Application Serial No. PCT/US2009/032706, Written Opinion mailed Nov. 27, 2009", 4 pgs.
"International Application Serial No. PCT/US2010/021528, Search Report mailed Aug. 31, 2010", 4 pgs.
"International Application Serial No. PCT/US2010/021528, Written Opinion mailed Aug. 4, 2011", 6 pgs.
"International Application Serial No. PCT/US2010/021528, Written Opinion mailed Aug. 31, 2010", 4 pgs.
"International Application Serial No. PCT/US2012/035484, International Preliminary Report on Patentability mailed Nov. 7, 2013", 8 pgs.
"International Application Serial No. PCT/US2012/035484, International Search Report mailed Aug. 23, 2012", 6 pgs.
"International Application Serial No. PCT/US2012/035484, Written Opinion mailed Aug. 23, 2012", 8 pgs.
"Japanese Application Serial No. 2010-545225, Amendment and Argument filed May 26, 2014 in response to Office Action mailed Jan. 29, 2014", w/English Claims, 11 pgs.

(56) References Cited

OTHER PUBLICATIONS

"Japanese Application Serial No. 2010-545225, Amendment and Argument filed Jun. 19, 2013 in response to Office Action mailed Dec. 20, 2012", w/English Claims, 10 pgs.

"Japanese Application Serial No. 2010-545225, Examiners Decision of Final Refusal mailed Sep. 29, 2014", w/English Translation, 4 pgs.

"Japanese Application Serial No. 2014-508606, Office Action mailed Oct. 20, 2014", 4 pgs.

"Korean Application Serial No. 10-2011-7019504, Notice of Final Rejection mailed Dec. 12, 2013", 4 pgs.

"Korean Application Serial No. 10-2011-7019504, Office Action mailed Apr. 26, 2013", 8 pgs.

"Korean Application Serial No. 10-2011-7019504, Office Action mailed Sep. 19, 2012", w/English Translation, 6 pgs.

"Korean Application Serial No. 10-2011-7019504, Response filed Aug. 26, 2013 to Office Action mailed Apr. 26, 2013", w/English Claims, 10 pgs.

"Korean Application Serial No. 10-2011-7019504, Response filed Sep. 18, 2014 to Notice of Preliminary Rejection mailed Apr. 18, 2014", w/English Claims, 32 pgs.

"Korean Application Serial No. 10-2011-7019504, Response filed Nov. 19, 2012 to Office Action mailed Sep. 19, 2012", w/English Claims, 22 pgs.

"Korean Application Serial No. 10-2011-7026540, Notice of Preliminary Rejection mailed Sep. 22, 2014", w/English Translation, 13 pgs.

Fontaine, N. H, et al., "Variable-angle internal-reflection Raman spectroscopy for depth-resolved vibrational characterization of polymer thin films", Phys. Rev. B, 57(7), (1998), 3807-3810.

Greene, P. R, et al., "Total internal reflection Raman spectroscopy of barley leaf epicuticular waxes in vivo", Colloids and Surfaces B: Biointerfaces, 45(3-4), (Nov. 10, 2005), 174-180.

Holzer, W., et al., "Raman study on surface layers and thin films by using total reflection experiments", Journal of Molecular Structure, 217, (Mar. 1990), 253-264.

Ishizaki, Fumihiko, et al., "Near-Infrared Attenuated Total Reflection Raman Spectroscopy for Polymer Surface Observation", Japanese Journal of Applied Physics, 47, (2008), 1621-1627.

Mckee, Kristopher J., et al., "Development of a scanning angle total internal reflection Raman spectrometer", Review of Scientific Instruments, 81(4), (2010), 043106-1-043106-6.

Rowell, N., et al., "Organic monolayers detected by single reflection attenuated total reflection infrared spectroscopy", Journal of Vacuum Science and Technology, Part A, 24(3), (2006), 668-672.

Tentori, D., et al., "High-Accuracy Critical Angle Refractometry", Optical Engineering, 32(3), (1993), 593-601.

"U.S. Appl. No. 13/098,140, Notice of Allowance mailed Dec. 16, 2014", 7 pgs.

"U.S. Appl. No. 13/145,711, Response filed Dec. 22, 2014 to Non Final Office Action mailed Jul. 24, 2014", 19 pgs.

"Australian Application Serial No. 2010234465, Response filed Oct. 10, 2013 to First Examination Report mailed Aug. 14, 2012", 18 pgs.

"Australian Application Serial No. 2013242819, Examination Report dated Jun. 6, 2014", 2 pgs.

"Canadian Application Serial No. 2,758,113, Office Action mailed Nov. 20, 2014", 3 pgs.

"Chinese Application Serial No. 201080025328,9, Response filed Jan. 3, 2014 to Office Action mailed Aug. 21, 2013", (w/ English Translation of Claims), 28 pgs.

"European Application Serial No. 10762403.3, Office Action Nov. 17, 2011", 2 pgs.

"European Application Serial No. 10762403.3, Response filed May 24, 2012 to Office Action Nov. 17, 2011", 5 pgs.

"International Application Serial No. PCT/US2009/032706, International Search Report mailed Nov. 27, 2009", 3 pgs.

"Japanese Application Serial No. 2012-504837, Amendment and Argument filed Jun. 4, 2014 in response to Office Action mailed Dec. 4, 2013", (w/ English Translation of Claims), 15 pgs.

"Korean Application Serial No. 10-2011-7026540, Amendment and Request for Consideration filed Aug. 21, 2014 in response to Notice of Final Rejection mailed May 21, 2014", (w/ English Translation of Claims), 18 pgs.

"Chinese Application Serial No. 201280020006.4, Office Action mailed Jan. 22, 2015", (w/ English Translation), 18 pgs.

"Korean Application Serial No. 10-2011-7019504, Final Office Action mailed Jan. 21, 2015", (w/ English Translation), 7 pgs.

\* cited by examiner

PERI-CRITICAL REFLECTION SPECTROSCOPY DEVICES, SYSTEMS, AND METHODS

CROSS-REFERENCE TO CLAIM OF PRIORITY

This patent application is a U.S. National Stage filing under 35 U.S.C. 371 from International Patent Application Serial No. PCT/US2010/030299, filed Apr. 7, 2010 and published on Oct. 14, 2010 as WO 2010/118175 A2, which claims the priority benefit of U.S. Provisional Application No. 61/167,505 filed Apr. 7, 2009, entitled Methods, Devices and Kits for Angle-Resolved Attenuated Reflection Spectroscopy, and U.S. Provisional Application No. 61/226,677 filed Jul. 17, 2009, entitled Methods, Devices and Kits for Angle-Resolved Attenuated Total Reflection Spectroscopy, the contents of which are incorporated herein by reference in their entirety.

BACKGROUND OF THE INVENTION

Internal reflection spectroscopy, also known as Attenuated Total Reflection (ATR) spectroscopy, has been know for many years, and is a widely used method of sampling in infrared (IR) and fluorescence spectroscopy, as well as in other spectroscopies. ATR is performed above the critical angle and results only in internal reflection. Mid-wavelength infrared (MWIR), or intermediate infrared (IIR), spectroscopy has over the years become a technique of choice when specificity is of utmost importance. It has historically been a difficult technique to use for several reasons. First, absorptivities of many materials are quite high in the mid-wavelength infrared region of the electromagnetic spectrum (e.g., from about 3-8 μm) While this is good from the standpoint of sensitivity, it makes sampling sometimes complex. As a result, a wide variety of sampling technologies have been developed to help introduce the sample to the spectrometer in an ideal fashion. A ubiquitous and problematic sample component is water. In the near-infrared (NIR) region, using wavelengths from about 800 nm to 2500 nm, another problem that can arise is the fact that the path length may be too short. One advantage is that near-infrared can typically penetrate much farther into a sample than mid infrared radiation. As a result, the literature advises that the critical angle should be avoided due to band distortions.

One problem faced when using spectroscopy is the fact that many sample preparations contain water. Water has a very high absorbance in the mid-infrared. Therefore, in order to measure a spectrum of water in the classical mid-infrared region of 4000-400 cm$^{-1}$, the path length must be limited to less than a few 10s of microns. ATR can provide this very small path length needed. In other situations however, the path length of ATR is too small for ideal sampling. This can be the main problem when trying to make measurements through mammalian skin or other biological tissue, or when the desired spectral information is from a deeper depth and not adjacent the surface of the mammalian skin.

Attenuated Total Reflection (ATR) is often indicated in difficult sampling situations. The spectroscopic usefulness of the effect was first noticed in the 1960s by Fahrenfort and is predictable from basic optical physics. Basically, when light propagates through a medium of high refractive index and approaches an interface with a material of lower refractive index, a transmission and a reflection will occur. The relative strengths of these transmissions and reflections are governed by the Fresnel equations:

$$r_\perp \equiv \frac{E_r}{E_i} = \frac{\frac{n_1}{\mu_1}\cos\theta - \frac{n_2}{\mu_2}\cos\theta'}{\frac{n_1}{\mu_1}\cos\theta + \frac{n_2}{\mu_2}\cos\theta'} \quad (1)$$

$$t_\perp \equiv \frac{E_t}{E_i} = \frac{2\frac{n_1}{\mu_1}\cos\theta}{\frac{n_1}{\mu_1}\cos\theta + \frac{n_2}{\mu_2}\cos\theta'} \quad (2)$$

$$r_\parallel \equiv \frac{E_r}{E_i} = \frac{\frac{n_2}{\mu_2}\cos\theta - \frac{n_1}{\mu_1}\cos\theta'}{\frac{n_1}{\mu_1}\cos\theta' + \frac{n_2}{\mu_2}\cos\theta} \quad (3)$$

$$t_\parallel \equiv \frac{E_t}{E_i} = \frac{2\frac{n_1}{\mu_1}\cos\theta}{\frac{n_1}{\mu_1}\cos\theta' + \frac{n_2}{\mu_2}\cos\theta} \quad (4)$$

The Fresnel equations give the ratio of the reflected and transmitted electric field amplitude to initial electric field for electromagnetic radiation incident on a dielectric.

In general, when a wave reaches a boundary between two different dielectric constants, part of the wave is reflected and part is transmitted, with the sum of the energies in these two waves equal to that of the original wave. Examination of these equations reveals that when the light is traversing through a high index medium and approaching an interface with a low index medium, the reflected component can be total, with no light being transmitted. The angle at which this occurs is called the critical angle and is defined by the following equation (5):

$$\theta_C = \sin^{-1}\left(\frac{n_2}{n_1}\right) \quad (5)$$

The reflected component has an angle of reflection equal and opposite to the angle of incidence upon the interface. Above the critical angle, all light is reflected. Below the critical angle, some light would transmit through the interface according to the above Fresnel equations. A device operating in this mode would use light that refracts according to Snell's Law (equation (6)):

$$n_1 \sin\theta = n_2 \sin\theta' \quad (6)$$

As previously stated, above the critical angle reflection is total. Fahrenfort first noticed that upon total reflection, a standing, or evanescent, wave is set up at the interface between high and low index. The wave has an exponentially decaying intensity into the rarer (lower index) medium. If an absorbing substance is placed in the vicinity of this evanescent (standing) wave, which extends a distance into the rarer medium, it can absorb portions of the light in specific wavelengths corresponding to the absorption properties of the material. In this way, the total reflection is said to be "frustrated" by the absorption of the sample. The returning light at the detector then is evaluated to determine the missing energy. It follows that this mode can be used to obtain an infrared spectrum of a material in contact with the high index medium through which the light is traveling. The strength of this interaction can be predicted through several equations developed by Harrick. First, the depth of penetration is defined as the 1/e point of the exponential decay of the evanescent (standing) wave (equation (7)):

$$d_p = \frac{\lambda/n_1}{2\pi\left(\sin^2\theta - \left(\frac{n_2}{n_1}\right)^2\right)^{\frac{1}{2}}} \quad (7)$$

where $n_2$ is the sample refractive index and $n_1$ is the crystal refractive index. The depth of penetration is defined as the point at which the strength of the evanescent wave electric vector decays to a value of 1/e (where e is Euler's number) from its original strength. Quick calculations are often done using the depth of penetration to characterize the strength of signal that will be obtained with ATR. The quick calculations may be less accurate but are suitable for providing a guide. A more accurate equation for the point where the evanescent wave electric vector decays was derived by Harrick, namely the effective thickness or effective depth, $d_e$.

An additional complication arises if the sample is thin compared to the 1/e point of the evanescent wave. The effective thickness calculation results in a number that can be used in Beer's Law calculations, and is closely related to the path length in a transmission measurement made at normal incidence. There are now three refractive indices to worry about: $n_1$, the index of the crystal, $n_2$, the index of the thin layer of sample, and $n_3$, the index of whatever is beyond the sample, usually air. Also, since the geometry is usually not near-normal, the calculation must be done for three orthogonal axes. Finally, the measurement is polarization dependent and should be calculated for two orthogonal polarizations. For purposes of this discussion, the thin layer is assumed to by isotropic and the polarization is deemed to be random. So the effective depth equation, for thin layers of sample where the sample layer thickness is much less than the depth of penetration, is as follows:

$$d_e = \frac{1}{\cos\theta}\frac{n_2}{n_1}\frac{d_p}{2}E_{02}^{r2}\cdot\left(\exp\left(-\frac{2z_i}{d_p}\right) - \exp\left(-\frac{2z_f}{d_p}\right)\right) \quad (8)$$

where the z values are the initial and final z-dimension positions of the film relative to the surface of the ATR prism. The E term is the square of the strength of the electric vector in medium 2 E is proportional to light intensity. For polarized incident light $$E_{02,\|}^{r2} = E_{02,x}^{r2} + E_{02,z}^{r2} \quad (9)$$

and $$E_{02,\perp}^{r2} = E_{02,y}^{r2} \quad (10)$$

and this results in $$d_{e,\|} = d_{ex} + d_{ez} \quad (11)$$

and $$d_{e,\perp} = d_{ey} \quad (12)$$

and $$d_{e,random} = (d_{e,\perp} + d_{e,\|})/2 \quad (13)$$

The three orthogonal electric field components are calculated from Fresnel's equations:

$$E_{0x,2}^{r} = \frac{2\cos\theta(\sin^2\theta - n_{31}^2)^{1/2}}{(1-n_{31}^2)^{1/2}[(1+n_{31}^2)\sin^2\theta - n_{31}^2]^{1/2}} \quad (14)$$

$$E_{0z,2}^{r} = \frac{2\cos\theta\sin\theta n_{31}^2}{(1-n_{31}^2)^{1/2}[(1+n_{31}^2)\sin^2\theta - n_{31}^2]^{1/2}} \quad (15)$$

and $$E_{0y,2}^{r} = \frac{2\cos\theta}{(1-n_{31}^2)^{1/2}} \quad (16)$$

In the equations immediately above, a thin film approximation is used, in order to greatly simplify the calculation of the field strength. As previously mentioned, Harrick proposed this approximation. The requirement to use this approximation is that the film must be very thin relative to the depth of penetration if the sample were infinitely thick. The depth of penetration for a thick film at 6 μm measuring wavelength would be 2.32 μm. A monolayer of anthrax spores, for example, would have a thickness of approximately 0.4 μm, so the thin film approximation is valid for early detection and identification of anthrax spores deposited onto an ATR prism. The values used in the above equations are as follows: $n_1=2.2$, $n_2=1.5$, $n_3=1.0$, $=45$, $z_i=0$. and $z_f=0.4$ m. Calculated values for the field strength are as follows: $E_{0x,2}^{r}=1.37$, $E_{0z,2}^{r}=0.79$, and $E_{0y,2}^{r}=1.60$. Calculated effective path for each vector are $d_{ex}^{iso}=0.45$ m, $d_{ey}^{iso}=0.62$ m, $d_{ez}^{iso}=0.15$ m, $d_{e,\|}^{iso}=0.60$ m, $d_{e,\perp}^{iso}=0.62$ m, and $d_{e,random}^{iso}=0.61$ m. The final value for effective thickness is therefore 0.61 μm.

A single reflection through the ATR system modeled here would give rise to a signal (at 6 μm wavelength) that is comparable to a layer of spores measured in transmission that is 0.61 μm thick, assuming a spore monolayer with a thickness of 0.4 μm. So the ATR technique, even in a single reflection, gives rise to a spectrum with 1.5× the strength of a transmission measurement. This figure can be increased dramatically by using multiple reflections, making ATR infrared an excellent identifier of biological warfare agents such as anthrax.

Other concepts relating to ATR spectroscopy are disclosed in, for example, U.S. Pat. No. 6,908,773 to Li et al. for ATR-FTIR Metal Surface Cleanliness Monitoring; U.S. Pat. No. 7,218,270 to Tamburino for ATR Trajectory Tracking System (A-Track); U.S. Pat. No. 6,841,792 to Bynum et al. for ATR Crystal Device; U.S. Pat. No. 6,493,080 to Boese for ATR Measuring Cell for FTIR Spectroscopy; U.S. Pat. No. 6,362,144 to Berman et al. for Cleaning System for Infrared ATR Glucose Measurement System (II); U.S. Pat. No. 6,141,100 to Burka et al. for Imaging ATR Spectrometer; U.S. Pat. No. 6,430,424 to Berman et al. for Infrared ATR Glucose Measurement System Utilizing a Single Surface of Skin.

Other references that may be of interest as well include KR 20060084499 A published Jul. 7, 2006, for Portable Biochip Scanner Using Surface Plasmon Resonance by Ok (published in the U.S. as US 2006/0187459 A1); U.S. Pat. No. 7,492,460 B2 issued Feb. 17, 2009, for Attenuated-Total-Reflection Measurement Apparatus by Koshoubu et al. (published as US 2006/0164633 A1); U.S. Pat. No. 6,417,924 B1 issued Jul. 9, 2002, for Surface Plasmon Sensor Obtaining Total Reflection Break Angle Based on Difference from Critical Angle by Kimura; U.S. Pat. No. 7,236,243 B2 issued Jun. 26, 2007, for Hand-Held Spectrometer by Beecroft, et al.; U.S. Publication US 2006/0043301 A1) published on Mar. 2, 2006, for Infrared Measuring Device, Especially for the Spectrometry of Aqueous Systems, Preferably Multiple Component Systems by Mantele et al.; and U.S. Publication US 2005/0229698 A1 published Oct. 20, 2005, for Hand-held Spectrometer by Beecroft, et al.

An often overlooked benefit of the ATR sampling mode for detecting and classifying samples, however, is the immunity to the effects of scatter. Harrick notes that the ATR mode, unlike transmission or regular reflection, removes the effect of light scatter. Even if a sample is granular in nature, a situation that normally would give rise to light scattering, the ATR spectrum will maintain a flat baseline. This means that different preparations of the same sample can be more similar to each other, and therefore easier to classify in the same group. If there exists real chemical differences between two samples, the differences are more easily discerned because the sample morphology, preparation, and packing are removed as variables. An advantage of ATR, often overlooked, is its immunity to the effects of scatter. A "perfect" infrared spectrum would contain only information related to the molecular structure of the sample. Sampling artifacts almost always are superimposed on this pure spectrum. However ATR can remove some of the differences due to sample scatter, improving the ability to identify and classify a sample. This can be a huge advantage in the area of tissue spectroscopy.

An interesting recurring theme in the spectroscopy literature is the admonition to stay away from the critical angle (*Internal Reflection Spectroscopy: Theory and Applications*, Francis M. Mirabella, CRC Press, 1993) because spectral distortions will result. This was noted early on in the seminal book by Harrick, and has been repeated many times since. The basis for this warning is seen in the depth of penetration equations listed above. As the angle of incidence gets smaller and approaches the critical angle, the depth of penetration of the evanescent wave into the rarer medium gets larger and larger, up until the critical angle, at which point the total internal reflection condition no longer holds. Below the critical angle, internal reflection turns into the much more common and much less useful external reflection. External reflection is also governed by the laws of Fresnel reflection, but the resulting reflection is no longer total. In external reflection, it is not possible to couple a large efficiency of energy back into the ATR prism and subsequently to the detector.

For many samples, it would be desirable to have a large depth of penetration into the sample. This could be achieved by introducing electromagnetic energy very close to a critical angle for the sample. In most spectrometers, the light beam has a significant angular dispersion, in order to fill the detector and obtain high signal-to-noise ratio (SNR). However, because there is much angular dispersion, as the critical angle is approached, a portion of the beam starts to exceed the critical angle, while another portion of the beam is still at an angle that is well away from the critical angle. In addition, in most samples there is dispersion in the refractive index across the spectral region of interest, and so the critical angle is different for different wavelengths. So these factors require the average angle to often be several degrees away from the critical angle.

It can be readily seen that the depth of penetration into the rarer medium can actually become quite large. There are many applications in which a larger depth of penetration would be desirable. The non-invasive measurement of body constituents is amongst these. The teaching, repeated many times in the literature, is that ATR can not have a large path length and can not have a large depth of penetration, because distortions of the spectrum occur near the critical angle. This problem could be overcome by the use of a highly collimated beam of light. Light sources are now available that can be highly collimated, yet still contain excellent amounts of energy. Many lasers such as quantum cascade lasers and light emitting diode (LED) sources are now available that can be highly collimated and still contain large amounts of energy. But this is not a complete solution to the problem.

Another problem that needs to be overcome is the fact that most samples themselves exhibit wavelength dispersion in their refractive index. If useful spectroscopic information about a sample is desired, whether by fluorescence, near infrared, terahertz, or some other spectroscopy, the signal should be collected over some range of wavelengths. It will almost certainly be true that over the wavelength range of interest, the critical angle will vary with wavelength. The critical angle will even change within the same sample depending on various characteristics of the sample, such as the sample morphology or the physical state of the sample. Therefore it is very difficult, if not impossible to know, a priori, where the critical angle will lie, for a given sample at a given wavelength. What is needed is an added dimension to the ATR measurement, namely that of a mapping of not only intensity versus wavelength, but of intensity versus wavelength versus angle of incidence and/or reflection.

An ATR sampler can be designed that allows for multiple reflections. Multiple reflections thereby multiply the strength of the infrared spectrum. The number of reflections can be adjusted to arrive at an optimum effective path length to give the highest possible signal-to-noise ratio. The apparatuses and methods described here provides for measurements that are at least one, and probably two, orders of magnitude more sensitive than making the measurement in a transmission mode or a traditional ATR mode. In order to successfully map the angular space of interest, it would be desirable to cross over the critical angle and also collect data below the critical angle. This data could be useful in determining a true critical angle for each wavelength.

SUMMARY OF THE INVENTION

An aspect of the disclosure is directed to an apparatus for detecting the spectral characteristics of a sample. An apparatus comprises: a source of electromagnetic radiation in at least a first wavelength and a second wavelength; a crystal having a high refractive index adapted to reflect the electromagnetic radiation in the at least first wavelength and second wavelength; a reflector adapted to introduce the electromagnetic radiation in the at least first wavelength and second wavelength to the sample at a location across a range of angles including a critical angle between the crystal and the sample; and a detector for detecting a return electromagnetic radiation from each of the at least first wavelength and second wavelength from the sample. Additionally the components of the apparatus can be configured to be contained within a housing. Suitable detectors for the apparatus include, but are not limited to, a single element detector, such as a mercury telluride detector, a linear array detector, and a 2-dimensional array detector. The electromagnetic radiation source can be adapted to deliver an electromagnetic radiation to the sample at an angle of incidence which is at or below the critical angle. In other configurations, the electromagnetic radiation delivered to the sample can be delivered such that it approaches and passes the critical angle. In other configurations, the radiation is delivered at an angle at or above the critical angle. This radiation can also be adjusted to be delivered in such a way that it approaches and passes the critical angle. Data processors can also be provided that are in communication with the detector. The data processors can be configured such that the data processor receives information from any of the components of the system and then generates a critical angle map of the sample from one or more electromagnetic radiation detections received by the detector from the sample. Suitable electromagnetic radiation sources include, for example, a quantum cascade laser. In some configurations, the apparatus is adapted to collimate the radiation. The apparatuses are configurable to be housed in an area less than 1 cubic foot in volume, less than 125 cubic inches in volume, and less than 8 cubic inches in volume. Suitable configurations are also adapted to be handheld. In other configurations, a display screen is provided. The display screen can be adapted and configured to display information useful to a user including, for example, the critical angle map. The data processor can be adapted to generate a full map of reflected light intensity versus wavelength versus a mapping of the angle of incidence from the detected electromagnetic radiation. Moreover, in some aspects, a drive mechanism can be provided. The drive mechanism can be adapted to pivot the crystal or prism about an axis. A cooler can also be provided. A cooler would be useful for cooling the detector. Additionally one or more filters can be provided and one or more lenses can be provided. Lenses can be configured to image the electromagnetic radiation onto a detector less that 1 mm squared.

Another aspect of the disclosure is directed to a method for detecting the spectral characteristics of a sample. The method comprises, for example, placing a sample in proximity to a crystal; emitting an electromagnetic radiation from an electromagnetic radiation source in at least a first wavelength and a second wavelength through the crystal at a fixed or variable angle of incidence; introducing the electromagnetic radiation in the at least first wavelength and second wavelength to the sample at a location through the crystal at an angle of incidence at or near a critical angle of the sample; and detecting a return electromagnetic radiation from the at least first wavelength and second wavelength from the sample.

Additionally, the method can include the steps of introducing the electromagnetic radiation at an angle of incidence below the critical angle; and increasing the angle of incidence of the electromagnetic radiation incrementally whereby the angle of incidence approaches and passes the critical angle. In some aspects of the method, the method can include the steps of introducing the electromagnetic radiation at an angle of incidence above the critical angle; and decreasing the angle of incidence of the electromagnetic radiation incrementally whereby the angle of incidence approaches and passes the critical angle. Additionally, the method can comprise or more steps of generating a full map of reflected light intensity versus wavelength versus a mapping of the angle of incidence; displaying a generated map; comparing the detected electromagnetic radiation to a database of critical angle measurements; displaying a detected electromagnetic radiation parameter and one or more critical angle measurements from the database; filtering the electromagnetic radiation; pivoting the crystal or prism about an axis; cooling the detector; and imaging the electromagnetic radiation onto a detector area less than 1 mm$^2$.

Other aspects include one or more networked apparatuses. The networked apparatuses comprise: a memory; a processor; a communicator; a display; and an apparatus for detecting spectral characteristic comprising a source of electromagnetic radiation in at least a first wavelength and a second wavelength; a crystal having a high refractive index adapted to reflect the electromagnetic radiation from the at least first wavelength and second wavelength; a reflector adapted to introduce the electromagnetic radiation in the at least first wavelength and second wavelength to the sample at a location across a range of angles including a critical angle between the crystal and the sample; and a detector for detecting a return electromagnetic radiation from each of the at least first wavelength and second wavelength from the electromagnetic radiation from the sample.

In some aspects communication systems are provided. The communication systems comprise: an apparatus for detecting spectral characteristic comprising a source of electromagnetic radiation in at least a first wavelength and a second wavelength; a crystal having a high refractive index adapted to reflect the electromagnetic radiation from the at least first wavelength and second wavelength; a reflector adapted to introduce the electromagnetic radiation in the at least first wavelength and second wavelength to the sample at a location across a range of angles including a critical angle between the crystal and the sample; and a detector for detecting a return electromagnetic radiation from each of the at least first wavelength and second wavelength from the electromagnetic radiation from the sample; a server computer system; a measurement module on the server computer system for permitting the transmission of a sample measurement from the system for measuring the characteristic of the sample over a network; at least one of an API engine connected to at least one of the system for measuring the characteristic of the sample to create a message about the sample measurement and transmit the message over an API integrated network to a recipient having a predetermined recipient user name, an SMS engine connected to at least one of the system for measuring the characteristic of the sample to create an SMS message about the sample measurement and transmit the SMS message over a network to a recipient device having a predetermined sample measurement recipient telephone number, and an email engine connected to at least one of the system for measuring the characteristic of the sample to create an email message about the sample measurement and transmit the email message over the network to a sample measurement recipient email having a predetermined sample measurement recipient email address. A storing module can also be provided on the server computer system for storing the sample measurement on the system for measuring the characteristic of the sample server database. Moreover, at least one of the system for measuring the characteristic of the sample is connectable to the server computer system over at least one of a mobile phone network and an Internet network, and a browser on the sample measurement recipient electronic device is used to retrieve an interface on the server computer system. Additionally, a plurality of email addresses are held in a system for measuring the characteristic of the sample database and fewer than all the email addresses are individually selectable from the computer system, the email message being transmitted to at least one sample measurement recipient email having at least one selected email address. In some instances at least one of the system for measuring the characteristic of the sample is connectable to the server computer system over the Internet, and a browser on the sample measurement recipient electronic device is used to retrieve an interface on the server computer system. Where the system is in communication with, for example, a healthcare provider a plurality of user names are held in the system for detecting spectral characteristics database and fewer than all the user names are individually selectable from the computer system, the message being transmitted to at least one sample measurement recipient user name via an API. The sample measurement recipient electronic device can also be connectable to the server computer system over the Internet, and a browser on the sample measurement recipient electronic device is used to retrieve an interface on the server computer system. The sample measurement recipient electronic device may also be connected to the server computer system over a cellular phone network, such as where the electronic device is a mobile device. Additionally, the system can include an interface on the server computer system, the interface being retrievable by an application on the sample measurement recipient mobile device. In some cases, the SMS sample measurement is received by a message application on the sample measurement recipient mobile device. Where a plurality of SMS sample measurements are received for the sample measurement, each by a respective message application on a respective sample measurement recipient mobile device. At least one SMS engine can be configured to receive an SMS response over the cellular phone SMS network from the sample measurement recipient mobile device and stores an SMS response on the server computer system. Additionally, a sample measurement recipient phone number ID is transmitted with the SMS sample measurement to the SMS engine and is used by the server computer system to associate the SMS sample measurement with the SMS response. Moreover, the server computer system can be connectable over a cellular phone network to receive a response from the sample measurement recipient mobile device. The SMS sample measurement can also include a URL that is selectable at the sample measurement recipient mobile device to respond from the sample measurement recipient mobile device to the server computer system, the server computer system utilizing the URL to associate the response with the SMS sample measurement. The communication system can further comprise in at least some configurations: a downloadable application residing on the sample measurement recipient mobile device, the downloadable application transmitting the response and a sample measurement recipient phone number ID over the cellular phone network to the server computer system, the server computer system utilizing the sample measurement recipient phone number ID to associate the response with the SMS sample measurement. In other configurations, the system can comprise: a transmissions module that transmits the sample measurement over a network other than the cellular phone SMS network to a sample measurement recipient user computer system, in parallel with the sample measurement that is sent over the cellular phone SMS network, and/or a downloadable application residing on the sample measurement recipient host computer, the downloadable application transmitting a response and a sample measurement recipient phone number ID over the cellular phone network to the server computer system, the server computer system utilizing the sample measurement recipient phone number ID to associate the response with the SMS sample measurement.

Other aspects include one or more networked apparatuses. The networked apparatuses comprise: a memory; a processor; a communicator; a display; and an apparatus for detecting the spectral characteristics of a sample comprising an electromagnetic radiation source adapted to excite a sample with electromagnetic radiation, a crystal in communication with the electromagnetic radiation source and the sample, the crystal having a high refractive index adapted to reflect the electromagnetic radiation, a reflector adapted to introduce the electromagnetic radiation to the sample at a location at an angle of incidence at or near a critical angle between the crystal and the sample, and a detector for detecting an electromagnetic radiation from the sample.

In some aspects the communication systems comprise: an apparatus for detecting the spectral characteristics of a sample comprising an electromagnetic radiation source adapted to excite a sample with electromagnetic radiation, a crystal in communication with the electromagnetic radiation source and the sample, the crystal having a high refractive index adapted to reflect the electromagnetic radiation, a reflector adapted to introduce the electromagnetic radiation to the sample at a location at an angle of incidence at or near a critical angle between the crystal and the sample, and a detector for detecting an electromagnetic radiation from the sample; a server computer system; a measurement module on the server computer system for permitting the transmission of a sample measurement from the system for measuring the characteristic of the sample over a network; at least one of an API engine connected to at least one of the system for measuring the characteristic of the sample to create a message about the sample measurement and transmit the message over an API integrated network to a recipient having a predetermined recipient user name, an SMS engine connected to at least one of the system for measuring the characteristic of the sample to create an SMS message about the sample measurement and transmit the SMS message over a network to a recipient device having a predetermined sample measurement recipient telephone number, and an email engine connected to at least one of the system for measuring the characteristic of the sample to create an email message about the sample measurement and transmit the email message over the network to a sample measurement recipient email having a predetermined sample measurement recipient email address. A storing module can also be provided on the server computer system for storing the sample measurement on the system for measuring the characteristic of the sample server database. Moreover, at least one of the system for measuring the characteristic of the sample is connectable to the server computer system over at least one of a mobile phone network and an Internet network, and a browser on the sample measurement recipient electronic device is used to retrieve an interface on the server computer system. Additionally, a plurality of email addresses are held in a system for measuring the characteristic of the sample database and fewer than all the email addresses are individually selectable from the computer system, the email message being transmitted to at least one sample measurement recipient email having at least one selected email address. In some instances at least one of the system for measuring the characteristic of the sample is connectable to the server computer system over the Internet, and a browser on the sample measurement recipient electronic device is used to retrieve an interface on the server computer system. Where the system is in communication with, for example, a healthcare provider a plurality of user names are held in the system for detecting spectral characteristics database and fewer than all the user names are individually selectable from the computer system, the message being transmitted to at least one sample measurement recipient user name via an API. The sample measurement recipient electronic device can also be connectable to the server computer system over the Internet, and a browser on the sample measurement recipient electronic device is used to retrieve an interface on the server computer system. The sample measurement recipient electronic device may also be connected to the server computer system over a cellular phone network, such as where the electronic device is a mobile device. Additionally, the system can include an interface on the server computer system, the interface being retrievable by an application on the sample measurement recipient mobile device. In some cases, the SMS sample measurement is received by a message application on the sample measurement recipient mobile device. Where a plurality of SMS sample measurements are received for the sample measurement, each by a respective message application on a respective sample measurement recipient mobile device. At least one SMS engine can be configured to receive an SMS response over the cellular phone SMS network from the sample measurement recipient mobile device and stores an SMS response on the server computer system. Additionally, a sample measurement recipient phone number ID is transmitted with the SMS sample measurement to the SMS engine and is used by the server computer system to associate the SMS sample measurement with the SMS response. Moreover, the server computer system can be connectable over a cellular phone network to receive a response from the sample measurement recipient mobile device. The SMS sample measurement can also include a URL that is selectable at the sample measurement recipient mobile device to respond from the sample measurement recipient mobile device to the server computer system, the server computer system utilizing the URL to associate the response with the SMS sample measurement. The communication system can further comprise in at least some configurations: a downloadable application residing on the sample measurement recipient mobile device, the downloadable application transmitting the response and a sample measurement recipient phone number ID over the cellular phone network to the server computer system, the server computer system utilizing the sample measurement recipient phone number ID to associate the response with the SMS sample measurement. In other configurations, the system can comprise: a transmissions module that transmits the sample measurement over a network other than the cellular phone SMS network to a sample measurement recipient user computer system, in parallel with the sample measurement that is sent over the cellular phone SMS network, and/or a downloadable application residing on the sample measurement recipient host computer, the downloadable application transmitting a response and a sample measurement recipient phone number ID over the cellular phone network to the server computer system, the server computer system utilizing the sample measurement recipient phone number ID to associate the response with the SMS sample measurement.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
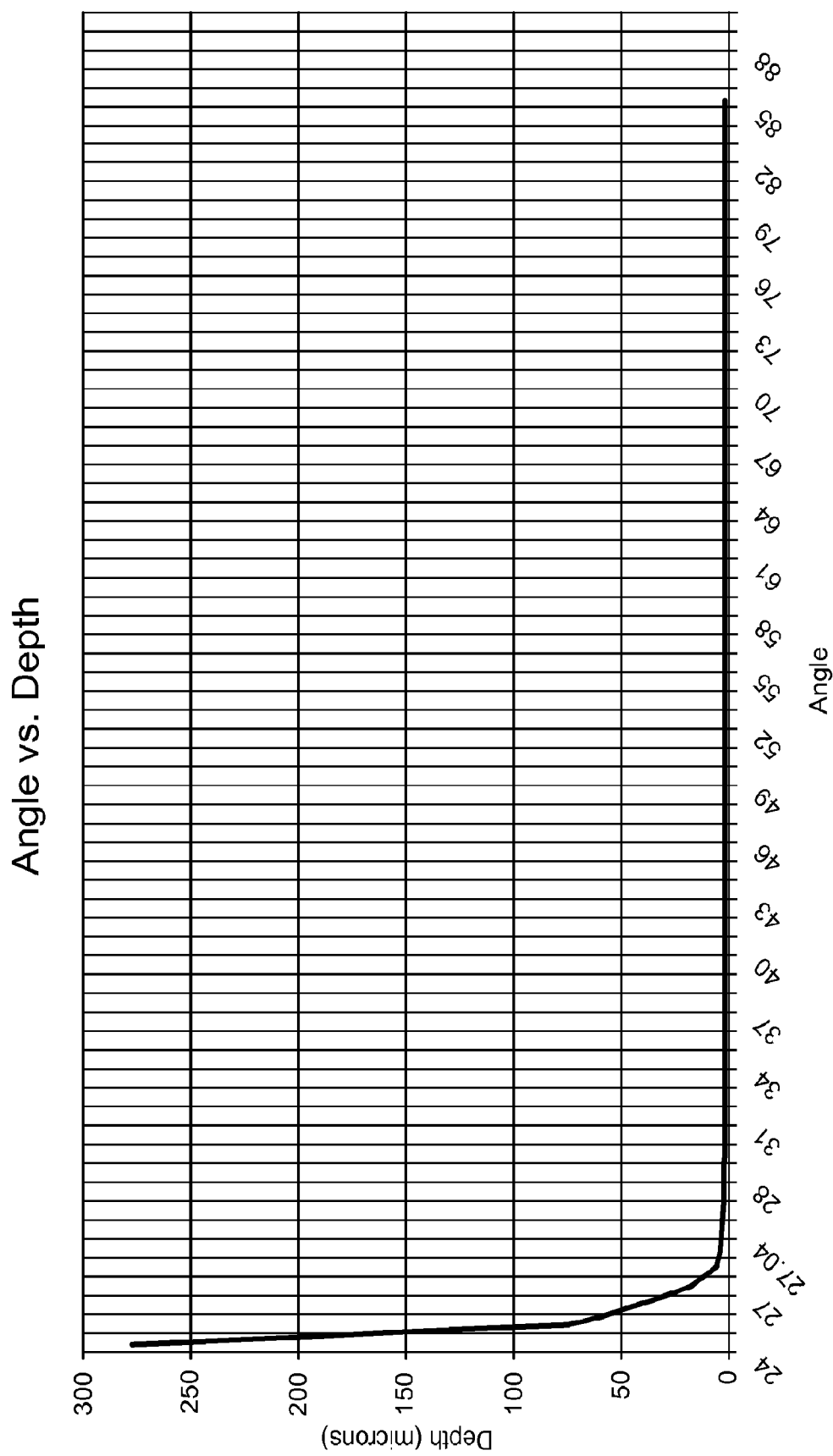
FIG. 1 is a graph showing the correlation between incident angle and the depth of penetration.

This invention therefore is directed toward the creation of devices and systems that generate a critical angle map of a sample in addition to a spectral absorption map. The invention provides an added dimension to the ATR measurement, by providing mapping of not only intensity versus wavelength, but of intensity versus wavelength versus angle of incidence and/or intensity versus wavelength versus angle of incidence reflection. The devices and systems can be configured such that one or more elements or components are formed integrally to achieve a desired physiological, operational or functional result such that the components complete the device. This can be achieved by one or more elements being integrally formed as a single piece or being formed to act in a unified manner. The region around the critical angle is a peri-critical region. Techniques useful to probe the peri-critical region include peri-critical reflection spectroscopy (PR).

Samples include, but are not limited to biological warfare agent detection, non-invasive transcutaneous detection of glucose, ethanol, cancer cells, and other medically relevant constituents, biomarkers, drug components for new drug discovery, detection of explosives and other harmful chemical agents, early detection of infectious diseases, detection of trace chemical or biological contaminants in drinking water, illegal drug detection, determining the quality of industrial chemicals during production including biofuels such as biodiesel and bioethanol, determining the progress of reactions taking place in bioreactors, in vitro detecting and quantifying constituents of blood such as glucose and creatinine. The maps are generatable with high angular resolution near the critical angle for each wavelength. In most instances, the angular resolution is at least a millidegree or better.

I. DEVICES AND SYSTEMS

A peri-critical reflection spectroscopy apparatus or system, is adapted to provide a source of electromagnetic radiation which can be introduced into a sample, such as those described above. The electromagnetic radiation can be modulated, for example, by an interferometer prior to contacting the sample. The modulated radiation can also be focused by a lens onto a reflective surface, such as a mirror, which then reflects the light into an ATR prism. Furthermore, in some instances, the mirror can be adjusted so that the electromagnetic radiation is introduced to the sample through a range of angles which encompasses a target critical angle. In other words, the electromagnetic radiation is introduced at an angle less than the critical angle and is swept in increments through the critical angle to an angle greater than the critical angle. The mirror can be adjusted to change the angle at which the electromagnetic radiation enters the sample. Alternatively the electromagnetic radiation can be introduced directly to the ATR prism. The electromagnetic radiation, once inside the ATR prism then comes into contact with the sample. The electromagnetic radiation then exits the prism and is detected by a detector and processed by a data processing system. The data processing system can be on the device or in communication with the device via, for example, a communication network or an interconnection device.

The critical angle information obtained using the systems and devices described herein is another dimension of information, which is not now obtained with existing technology. The devices are adapted and configured to measure the propagating light field. From this measurement a complete map of a sample can be determined. The complete map would therefore be a full map of reflected light intensity versus wavelength versus a mapping of the angle of incidence, at angles that approach and then in fact somewhat cross over, the critical angle. An angular resolution of a few millidegrees (a few microradians) is necessary, because, as illustrated in FIG. 1, the depth of penetration is very sensitive to the angle of incidence around the critical angle. Additionally, a processor, either on the device or in communication with the device, can be used with the device to analyze the critical angle data.

Once an angular map of the sample is generated by, for example, scanning the sample, the actual angle of the critical angle for the each wavelength can be determined. A spectrum at each wavelength at a constant effective depth can then be plotted.

Figure 2:
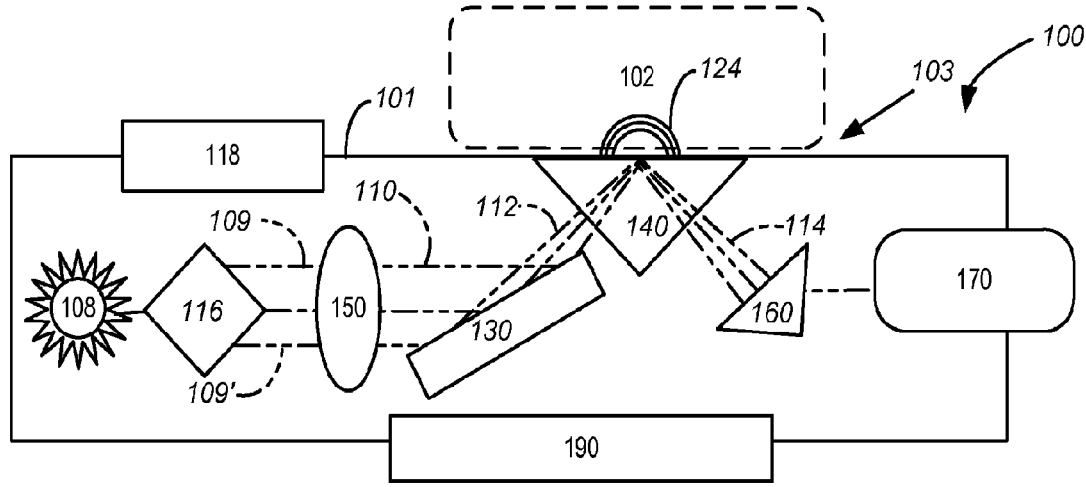
FIG. 2 is an illustration of a peri-critical reflection spectroscopy system.

FIG. 2 is an illustration of a peri-critical reflection spectroscopy device 100. A power source 118, which may be removable, adapted and configured to provide power to the system for electromagnetic radiation or light to be delivered from an electromagnetic radiation source 108 to an interferometer 116, which separates the beam of light received from the electromagnetic radiation source 108 into two or more beams of light 109, 109', such as by any suitable mechanism of reflection or means of reflection, and thereafter brings the rays together to produce interference. Suitable electromagnetic radiation sources can include, for example, an optical head that uses two or more quantum cascade lasers. The light can be from one or more sources which can be simultaneous or sequential. The power source 118 can be removable, rechargeable, or fixed (as in the case of a power cord). Suitable power sources include, but are not limited to, batteries. Moreover, power can come from an auxiliary device that the peri-critical reflection spectroscopy system is connected to such as a computer or mobile phone. Additionally, a microcontroller can be provided on the device in order to facilitated manipulation and analysis of the information obtained from the sample. Alternatively, the information can be transmitted to a secondary device for manipulation.

As will be appreciated by those skilled in the art, the system can be contained within a suitably designed housing 101 or the components can be configured such that the components are interconnected in such a way as to function as a housing.

After passing through a lens 150, a resulting beam 110 then comes in contact with a mirror 130. The mirror reflects a resultant beam 112 through a prism 140 and towards a sample 102. The prism 140 is typically configured with respect to the device or housing such that a face of the prism can achieve direct contact with the sample 102 at an interface 103 between the prism and the sample. At the sample/prism interface 103, the beam or beams can interact with the sample 102. Thus, for example, we above the critical angle, the propagating beam reflects totally and a weak standing wave 124 interacts with the sample, probing to a small depth beyond the sample/prism interface 103. Well below the critical angle, the beam or beams can transmit into the sample and then reflect back via diffuse reflection. In the peri-critical region around the critical angle, there is a combination of these effects. Thus, there is a much stronger standing wave 124 which can penetrate deeply into the sample allowing measurement tens of wavelengths deep into a sample.

A reflected second beam 114 passes back through the prism 140 where it is received by a multi-element detector 160. The detector 160 can be adapted and configured to resolve an angle of incidence for the pixels to achieve a resolution of a millidegree or better. The detector pixels will each receive light that interacted with the sample at a slightly different angle of incidence. Some pixels will see light that was above the critical angle and some will see light that was below the critical angle. There will be one pixel that is receiving light at a very small distance away from the critical angle and this detector will be most useful in measuring deeply into the sample. The other pixels will see light that penetrated less deeply into the sample, and these pixels are used to subtract out the less deep and less important information. The detectors could be pyroelectric. Moreover, the pixels resolve angle of incidence with a resolution of a millidegree or better within the multi-element detector. The resolved pixels are then analyzed using a suitable data processing device or chip 170 or the data can be communicated to a second device such as a computer or mobile phone with has suitable data processing capabilities (as discussed more fully below). The analysis can include, for example, comparing the data against a library of data to determine a variance of the detected signal to a known sample. Additionally, the system can optionally include a display 190, such as a liquid crystal display (LCD), adapted to provide a display to a user of the full map of reflected light intensity versus wavelength versus a mapping of the angle of incidence.

As will be appreciated by those skilled in the art, connectivity can also be provided which enables the system to send the information to a printer, or a network. Connectivity can be, for example, wirelessly via the internet as well as via suitable connection ports.

Figure 3:
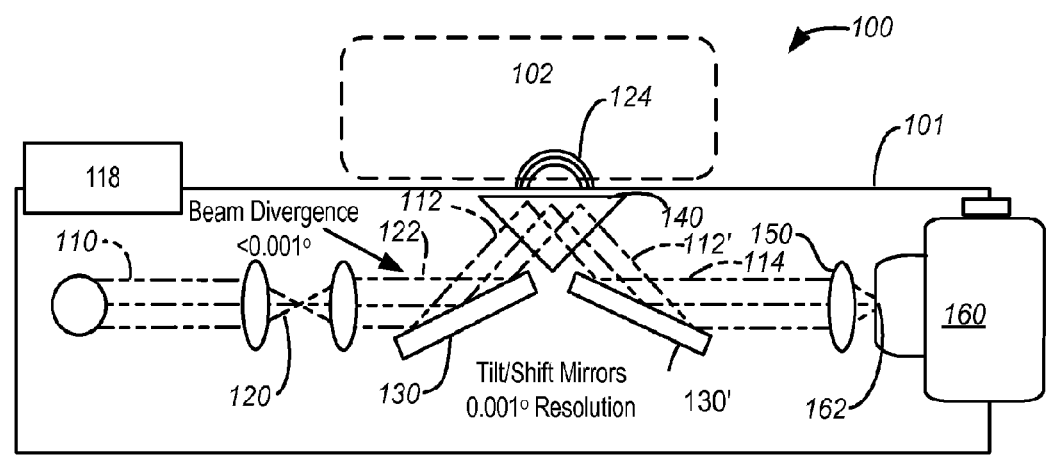
FIG. 3 is an illustration of a peri-critical reflection spectroscopy system.

The peri-critical reflection spectroscopy apparatus or system can be constructed as shown in FIG. 3. As with the previous configuration, power source 118, which may be removable, adapted and configured to provide power to the system. In FIG. 3, the spectroscopy apparatus 100 is set-up such that the electromagnetic radiation is introduced by a beam 110 to a sample 102 using a mirror 130, such as a tilt/shift mirror having a 0.001 degree resolution. The beam 110 can be delivered to the sample 102 after being passed through a spatial filter 120. Passing the beam 110 through the filter 120 can result in a small beam divergence, typically 0.001 degree. After passing through the filter 120, the highly collimated, small divergence beam 122 comes in contact with a tilt shift mirror 130 which deflects the beam through a peri-critical reflection (PR) crystal 140 against the sample 102. Suitable samples can, for example, have a same area as low as 1-10 mm in diameter. After the beam comes in contact with the same, a resulting beam 112 is reflected. The resultant beam 112' can then pass back through the PR crystal 140 to contact a second tilt/shift mirror 130' which transmits the resultant beam 114 through a lens 150 and into a small area single element mercury cadmium telluride (MCT) detector 160. Additionally, a display can be provided on the device, if desirable. As the angle of mirrors 130 130' are changed, the angle of incidence of the light at the sample/prism interface 103 changes. The angle is changed so that a range of angles including the critical angle is acquired. As one or both mirrors tilt, the different angles of incidence impinge on the small area detector 162. This critical angle map can then be used to determine the signal that coincides with the critical angle for the particular sample under test at the particular wavelength of light in use. In the peri-critical region, a strong standing wave 124 is created that can interact deeply into the sample.

A peri-critical reflection (PR) spectroscopy instrument configured as shown in FIG. 3 can include a spatial filter 120 of variable size that allows the infrared (IR) beam having one or more wavelengths from 750 nm to 100 μm an to be collimated to a desired angular resolution. The resulting collimated beam has nearly parallel rays. As a result of collimating, a beam divergence of as small as 1 millidegree is achievable. Launch mirrors 130, 130' can then be configurable such that the mirrors can tilt and shift to vary the angle of incidence on the sample. For example, the angle can be varied in order to cross over a critical angle for all wavelengths. A lens 150 can then be configured to image the spatial filter onto a very small detector area 162. Suitable areas include areas less than 1 $mm^2$, less than 0.01 $mm^2$, and more preferably less than 0.001 $mm^2$. The small area detector enables sensitivity improvement in systems that are limited by detector noise that usually dominate during experiments in the mid-infrared spectroscopy range.

The device and system can also be adapted and configured such that either or both of the mirror(s) and prism move or remain stationary relative to the sample. However, maintaining a fixed position would be a more practical configuration. In such cases an electromagnetic radiation source with a less collimated beam of energy can be used. Also, instead of sweeping the beam through a range of angles, the angular measurements can be made using a multiplicity of detectors (arrays) in such a manner such that each detector pixel element senses a progressively smaller (or larger) angle, such angle to include the critical angle at all wavelengths of interest. This detector array can be deployed after the sample and needs to be only a linear array of detector elements. Since it is often not possible to know beforehand what the critical angle will be at all of the wavelengths of interest, a detector containing a large number of pixels can be used. Otherwise, as previously described, the entire critical angle space could be mapped by sweeping the beam through different segments or portions of the total critical angle space in need of mapping.

In some instances the detector 160 can be cooled if desired for better sensitivity. Cooling is achievable using a suitable cooling apparatus, means for cooling, or cooling material. For example, cooling with liquid nitrogen may, in some instances, improve sensitivity of the detector. Cooling typically involves decreasing the temperature of the detector semiconductor material to the temperature of liquid nitrogen and most preferably to the temperature of liquid helium.

The beam generated by the system may be an output beam of a Fourier Transform Infrared (FTIR) spectrometer. However, as will be appreciated by those skilled in the art, a beam from a single or series of quantum cascade (QC) lasers may also be used. In some instances, selection of a beam type or source can improve the portability of the devices or systems. Thus, for example, a system less than 1 cubic foot in volume can be transported easily, and a system less than 125 cubic inches in volume can be handheld, and a system less than 8 cubic inches in volume may be concealed and hidden from view. This scalability of size provides significant advantages. Moreover, QC lasers can be highly collimated because their energy is emitted from a very small aperture.

The lasers and detectors can be on arms of a goniometer that enables movement in opposite directions, similar to a pendulum, as the device sweeps through an angle of incidence. Piezo electric motion devices can also be used.

In one aspect two different lasers can be used with two different detectors. In such a configuration both lasers can be configured to travel through the prism at the same time. The lasers would be separated by angular separation as the laser sweeps through the angles during operation. Alternatively, the electronics can be designed to operate two lasers such that the lasers emit in an alternating pattern and not simultaneously.

Alternative to using a multi-element detector, the angle of incidence of the beam may be changed manually and successive scans made. The input and the output angle may be changed together in order to obtain a complete map of the spectral data at the entire range of angle of incidences.

The angles interrogated should extend both above and below the expected critical angle. This is because the critical angle varies as a function of wavelength. The goal is to re-create a spectrum as a constant and known degree of closeness to the critical angle, or constant effective depth. In this manner, spectral distortions normally associated with working too close to the critical angle are completely obviated. It is now possible to collect undistorted spectra, while working very close to the critical angle. This allows the ATR method to have longer path length and deeper penetration into the rarer medium (the sample under test) than is possible using conventional methods. This will be particularly important in non-invasive biological measurements and many other measurements such as: detection of low levels of biological warfare agents.

Figure 4:
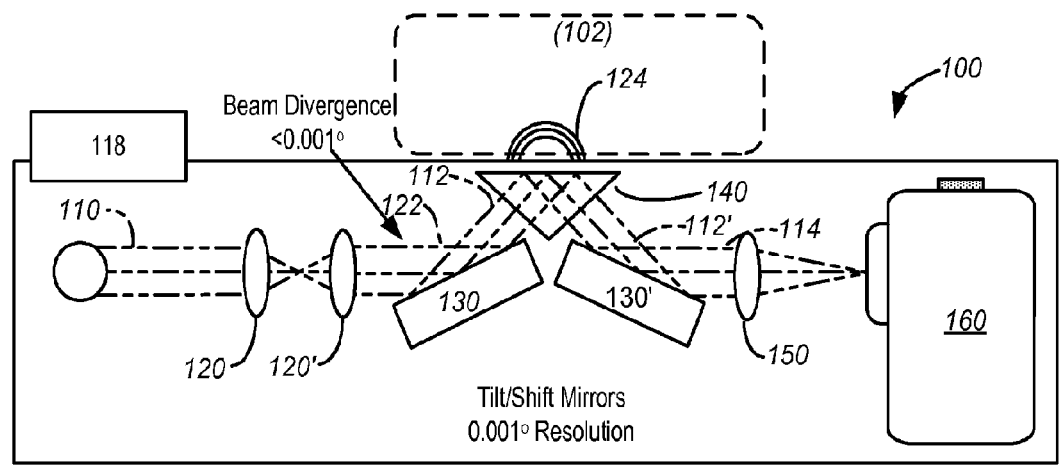
FIG. 4 is an illustration of a peri-critical reflection spectroscopy system showing imaging capability.

Turning to FIG. 4, an illustration of a peri-critical reflection spectroscopy system 100 is provided showing imaging capability. A beam 110, after passing through two filters 120, 120', the beam 122 comes in contact with a first tilt shift mirror 130 which deflects the a resulting beam 112 through a peri-critical reflection (PR) crystal 140 into the sample 102. The resultant beam 112' can then pass back through the PR crystal 140 to contact a second tilt/shift mirror 130' which transmits the resultant beam 114 through a lens 150. In this embodiment, the crystal 140/sample 102 surface is imaged onto an Array MCT detector 160 instead of the spatial filter, as illustrated above. The previous single element detector is replaced with a one- or two-dimensional detector array, as desired. A two-dimensional detector array can be adapted and configured to collect hyperspectral data with one dimension of wavelength, 2 dimensions of image and the further one dimension of angle of incidence. Each of these dimensions can, as will be appreciated by those skilled in the art, have thousands of data points. The depth of profiling capability of this system and technique allows for the creation of a three-dimensional spatial profile of a sample volume with spectral information at each spatial position. The multiple detectors have the effect of reducing the time needed to collect a data set, directly in proportion to the number of detector elements. Additionally a sample 102 area of 1-10 mm in diameter can be used. As with previous embodiments, a power source 118 can be provided along with an optional display.

Figure 5:
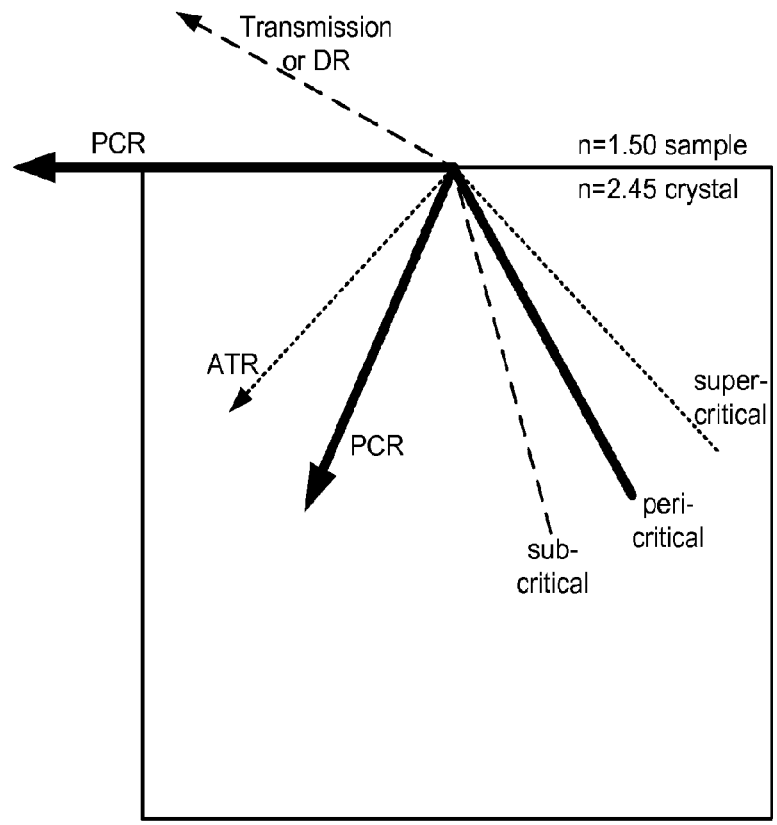
FIG. 5 is graph illustrating different effects achievable by changing an angle of incidence during spectroscopy.

FIG. 5 is graph illustrating different effects achievable by changing an angle of incidence during spectroscopy using the devices disclosed herein. Light rays are launched into a high index, or dense medium. Well below the critical angle (sub-critical), light refracts at the crystal/sample interface (e.g., the interface 103 in FIG. 2) and then mostly transmits into the sample itself as a propagating wave. If the sample is scattering, then diffuse reflection (DR) is the result. Well above the critical angle (super critical) light reflects totally and a weak standing or evanescent wave is set up in the rare medium (sample). As a result, no light waves propagate in the sample. The characteristics of the resulting sample spectrum is consistent with attenuated total reflection (ATR). Immediately in the vicinity of the critical angle (peri-critical), depth of penetration becomes very sensitive to angle. At the crystal/sample interface, three things happen: light reflects at the negative critical angle, a strong evanescent wave is set-up in the sample, and a traveling wave propagates in a direction parallel to the crystal sample interface plane. This effect benefits peri-critical reflection (PR) spectroscopy. By resolving angles accurately, to a millidegree, it is possible to map the peri-critical region for all wavelengths and refractive indices present in the given sample and crystal. The reflected PR beam contains strong information about the sample and from deeper depths into the sample than is possible by ATR.

Figure 6:
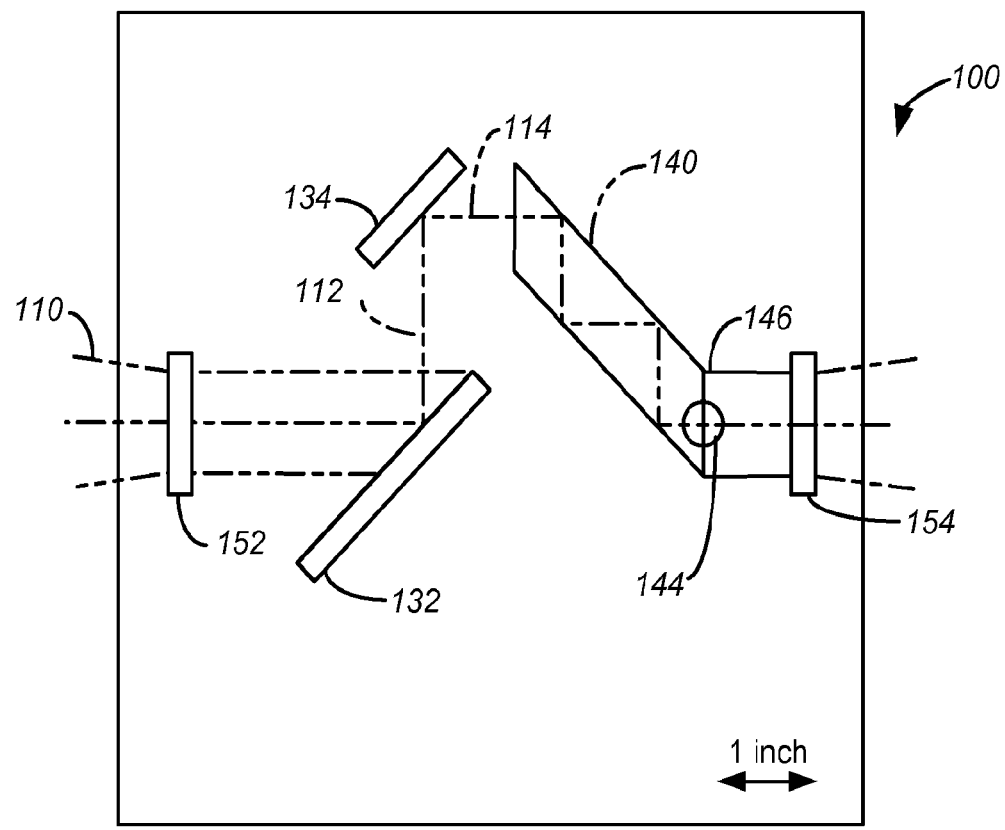
FIG. 6 is an illustration of another peri-critical reflection spectroscopy system wherein multiple reflections are achievable.

Turning now to FIG. 6, an illustration of another peri-critical reflection spectroscopy system 100 wherein multiple reflections are achievable is provided. A beam 110 from an electromagnetic radiation source passes through a negative lens 152 and hits a first mirror 132. The beam 110 is deflected from the first mirror 132, forming a resultant beam 112. The resultant beam 112 then hits a second mirror 134 and forms a second resultant beam 114, which comes in contact with a peri-critical reflection crystal or prism 140. The second resultant beam passes through the PR crystal from which it is then passes through a negative lens 154. Multiple reflections are achieved which are all at or near the critical angle. A precision drive (not shown), or any suitable means to move or rotate the platform or mechanism to move or rotate the platform, causes a platform to rotate or move. The platform carries first mirror 132, second mirror 134, and the PR crystal 140. The drive enables, for example, the platform to pivot around a pivot point 144 situated at or near an exit face 146 of the crystal 140. The negative lenses 152, 154 allow the instrument to be used in the sample compartment of many FTIR spectrometers that have a focusing beam near the center of the sample compartment. An example of a suitable FTIR device would be any Thermo Nicolet FTIR (Thermo Fisher Scientific, Waltham Mass.). The negative lenses collimate the beam, allowing angular resolution of the resulting collimated beam. Beam divergence, can further be limited by the J-stop (Jacquinot stop or field stop) inside the spectrometer, usually near the source. The beam divergence of the electromagnetic or IR beam is determined by an angular measurement of an increase in beam diameter over a distance from the source, or optical aperture.

Figure 7:
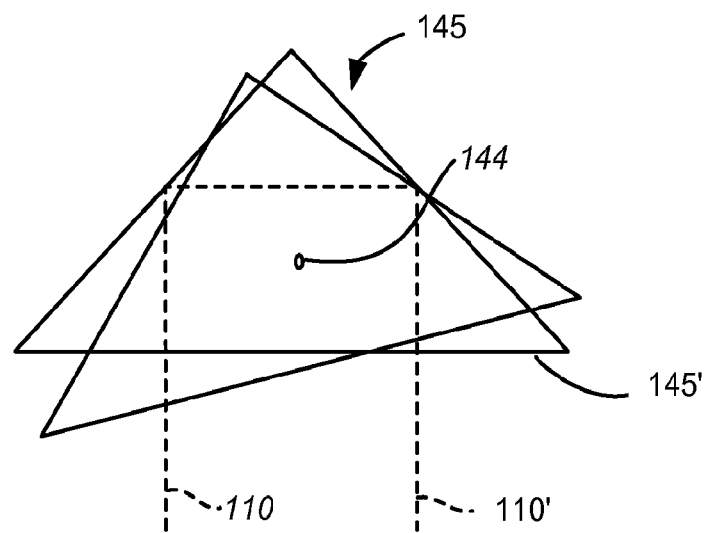
FIG. 7 illustrates a mechanism for changing an angle in a peri-critical reflection spectroscopy system.

As illustrated in FIG. 7, a mechanism for changing an angle in a peri-critical reflection spectroscopy system can be achieved. A 45 degree prism 145 made of a high index crystal, such as zinc selenide (ZnSe), can be used. The beam is launched in and out of the bottom face 145' of the prism 145 such that a first beam 110 enters the bottom face 145' of the crystal and a second beam 110' departs the bottom face 145' of the crystal parallel or substantially parallel to the first beam 110. The internal reflections of the beam occur at two facets of the prism following the path illustrated by the dashed line. Thus the incoming first beam 110 perpendicularly enters the bottom face 145' of the crystal, hits a facet of the prism where it is deflected at an angle of 90 degrees. The deflected beam then hits a second facet within the prism where it is deflected a second time at an angle of 90 degrees. The second deflected beam 110' then exits perpendicularly through the bottom face 145' of the crystal such that the incoming first beam 110 and departing second beam 110' are substantially parallel. The prism can be tilted about a pivot point 144. As a result of tilting the prism 145 around the pivot point 144, the angle of incidence on one facet increases while the angle of incidence on the other facet decreases. The sample under test can be adjacent to, or adhered to, one facet or the other of the prism. The input and output beams remain parallel to each other as the prism tilts. The ability to tilt the crystal while retaining parallel beams minimizes a need for re-alignment where there is an angle change.

Figure 8:
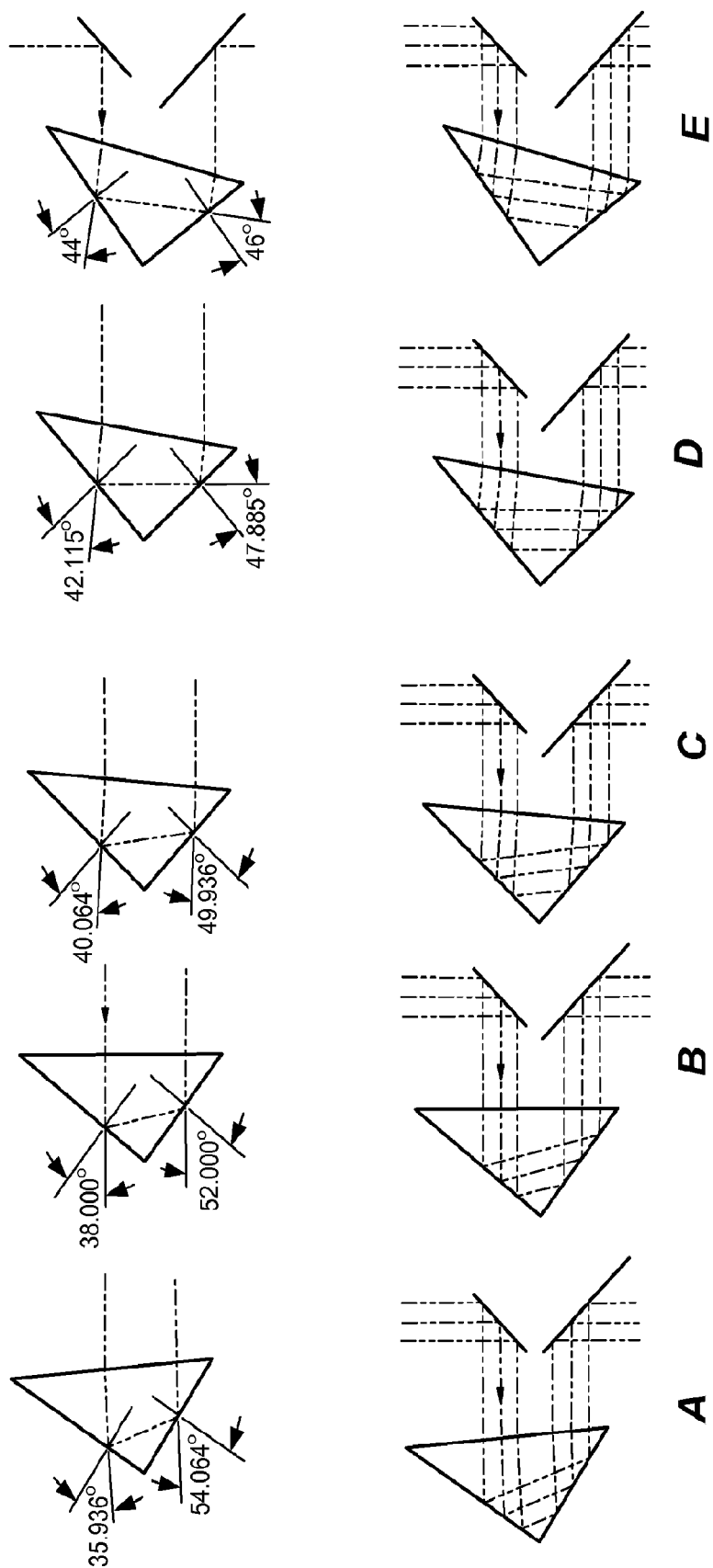
FIG. 8 illustrates a 45 degree prism moving through various angles of incidence.

Turning now to FIG. 8, a 45 degree prism shown on a top line moving through five separate sample angles of incidence (A-E). The prism retains the parallel beams as shown in the bottom line and as described above. Thus, an angular range of up to 10 degrees or more can be useful in PR spectroscopy.

As will be appreciated by those skilled in the art, devices according to this disclosure can have a variety of form factors and shapes. In some applications a small form factor, such as a form factor having a volume less than 5 $cm^3$ would be desirable, more preferably a volume less than 4 $cm^3$, or even more preferably a volume less than 3 $cm^3$, or any value less than 5 $cm^3$ to a measurement of about a $10^{th}$ of a cm.

II. METHODS

Figure 9:
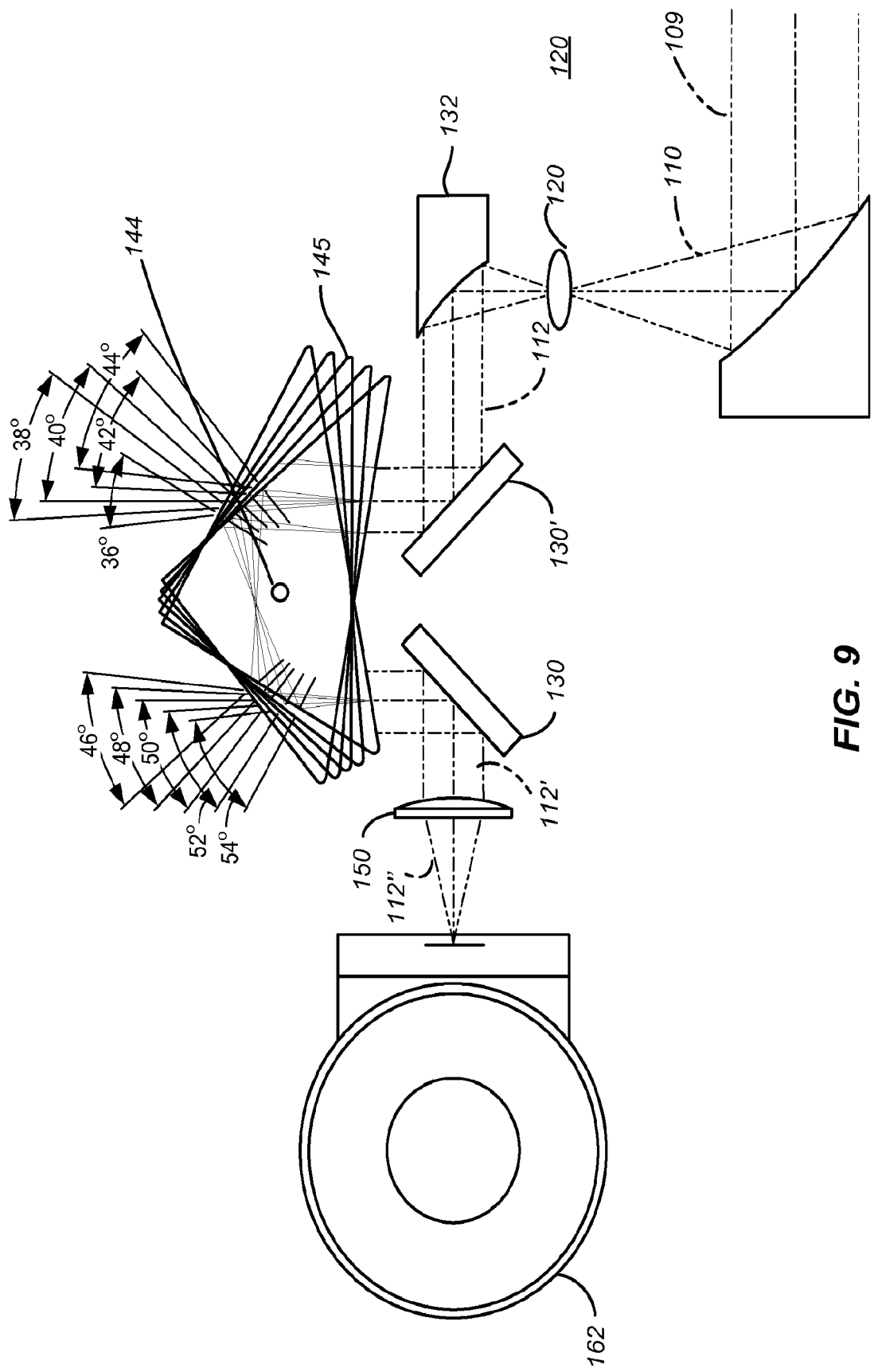
FIG. 9 illustrates an overview of a complete sampling system for spectroscopy.

FIG. 9 illustrates an overview of a complete sampling system for spectroscopy. The sampling system employs the previously described 45 degree prism. In this configuration, a pivot point is found that makes the input and output beams remain stationary during crystal tilting. As will be appreciated by those skilled in the art, the crystal is depicted with long facet and a short facet. A collimated beam 109 from an FTIR spectrometer is applied from a source to a reflective surface. The resulting beam 110 then travels through a spatial filter 120 and thereafter comes in contact with a collimating mirror 132. The resulting beam 112 is reflected toward a mirror 130' which then transmits the beam through a tilting prism 140 which pivots around a pivot point 144. Once the beam passes through the tilting prism into a sample, a return beam is picked up by a second mirror 130 and a resultant beam 112' is transmitted to a detector focusing lens 150 which then transmits a focused beam 112" to a detector 162.

Figure 10:
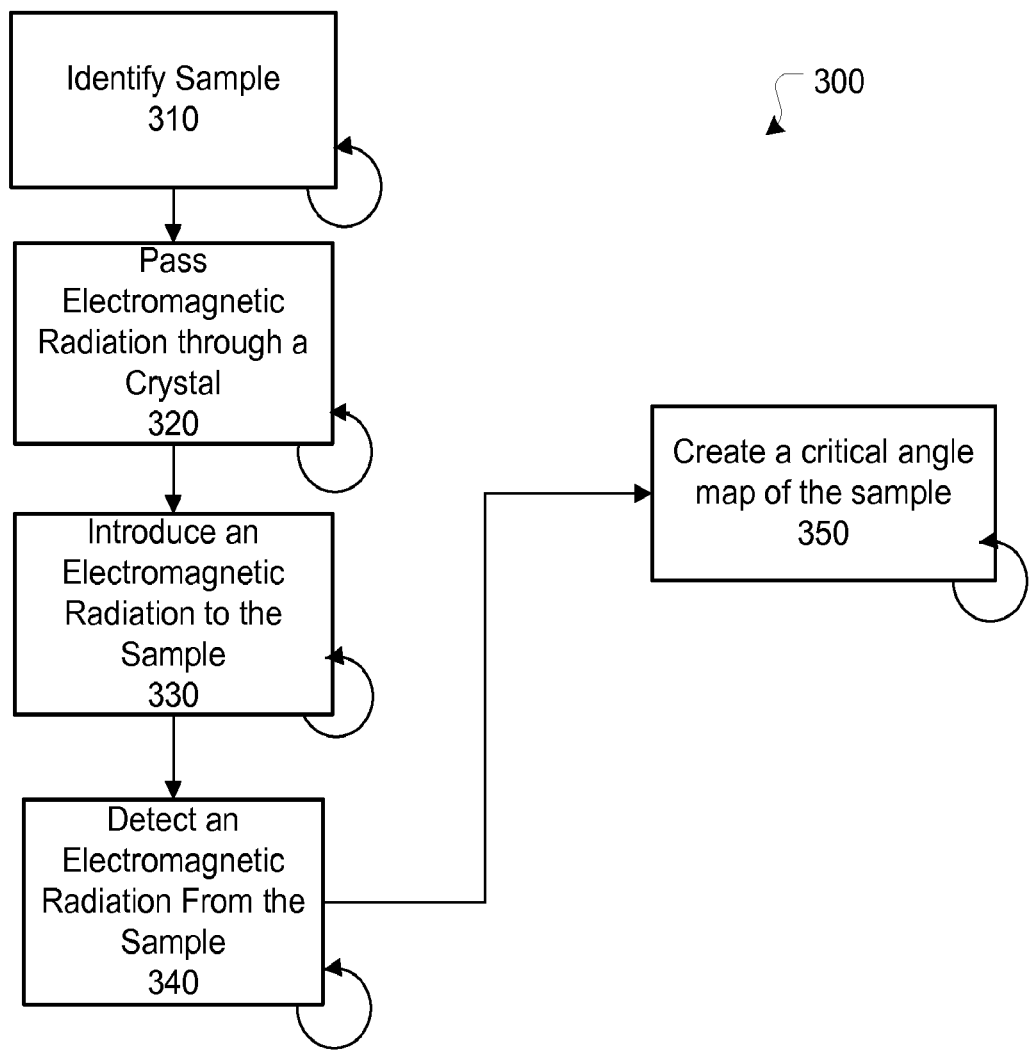
FIG. 10 is a flow chart illustrating methods of using the device.

As illustrated in FIG. 10, the basic steps of a method according to this disclosure include, identifying a sample 310. Passing electromagnetic radiation through a suitable crystal 320. Thereafter, introduce the electromagnetic radiation to the sample 330. A component of the electromagnetic radiation is capable of passing into and/or through a portion of the sample depending on the nature of the sample. After interacting with the sample, an electromagnetic radiation beam is transmitted back to the device from the sample 340. From the information that is transmitted back, a critical angle map of the sample can be created 350. One or more of these steps can be repeated, as desirable.

Typically, the device is measuring the propagating light field not the electromagnetic field. So, for example, when the sample is tissue, if no there was no tissue present then 100% of the signal would be received back. Detecting the difference in the resulting signal is then analyzed to determine characteristics of the sample. The method involves stepping through the angles, as appreciated from the disclosure above, because going through the angles assists in identifying the location of the critical angle, which can be impacted by a variety of parameters such as temperature and concentration. This enables a map of the critical angle to be created heuristically.

In other aspects of the disclosure, ATR spectroscopy instruments can be built to use either a fixed angle of incidence, or an angle that may be varied to detect a peri-critical reflection. As an angle of incidence is reduced toward a critical angle, the depth of penetration of an evanescent wave into the sample increases. This fact makes it possible to perform depth profiling spectroscopy into a sample. Spectral data is collected at a range of angles. By subtracting the shallower depth spectrum from the deeper depth spectrum, the spectrum of a deeper layer may be obtained. This capability is especially useful for the study of multiple-layer polymer films. The second reason for varying the angle of incidence is to measure the optical constants, n and k, of a sample. A set of spectra collected at variable angle can be used to find a baseline point for the Kramers-Kronig transform which when applied results in the estimation of n and k for all wavelengths. But a common problem in spectroscopy relates to quantitative analysis of materials. Quantitative analysis of substances in a sample if often achieved by measuring a range of samples in which the concentration of the substance is varied, and then building a multivariate model that describes the relationship between the set of spectra and the concentration(s) of the substance(s). The process of building these models of chemical systems using spectra or other physical properties of samples and substances is called chemometrics. A problem that needs to be overcome is that the chemometric models never report a perfectly accurate representation of the substance concentration. There is always an error term, often expressed as the SEP, or standard error of prediction. The problem is that this error term is often too large and prohibits a practical application of the model from accurately predicting the concentration of the substance or substances in the sample. What is needed is an added dimension to an ATR measurement, namely that of a mapping of not only intensity versus wavelength, but of intensity versus wavelength versus angle of incidence and/or reflection. In this manner, the accuracy of the model may be improved.

The variable angle ATR measurement is very sensitive to angle, and the beam of many spectrometers contains a large range of angles. For instance the sample compartment beam of a typical FT-IR spectrometer has a beam divergence of plus or minus 5 degrees. In the case of variable angle ATR measurements, a difference in angle of only a millidegree (0.001 degree) makes a significant difference in the coupling of the evanescent wave and thereby the depth of penetration measured. This is a problem that needs to be overcome. It is possible to pseudo-collimate the spectrometer beam, however in doing so, the beam diameter becomes quite large, and this is inconsistent with being able to build a compact instrument. In addition, the pseudo-collimated beam still has too large of a beam divergence. What is needed is a brighter, smaller light source so that the light can be efficiently collimated into a smaller diameter bundle, but still contain sufficient energy in order to make a spectroscopic measurement with high signal-to-noise ratio. A quantum cascade (QC) laser is a very small, bright light source. The exit aperture of a typical QC laser is on the order of a few microns, and can therefore be collimated into a bundle with little divergence using either an off-axis parabolic mirror or a simple aspheric lens. These QC lasers are readily available and can be combined with the variable angle ATR system. In this manner, a high degree of angular and depth resolution is obtained with higher brightness than is possible with the traditional infrared light source. In order to improve the SNR even further, a different type of detector is needed. Because of the high modulation frequency of FT-IR spectrometers, it has been impossible to use highly sensitive room-temperature detectors such as bolometers and thermopiles as detectors. Instead, triglycine sulfate detectors and their derivatives have been used. However, thermopile detectors can be 100 times more sensitive. This is a problem that needs to be overcome. The QC laser as a spectrally resolved light source has no need to be modulated rapidly, and therefore can be an excellent for performing variable angle ATR spectroscopy using thermopile detectors. The QC laser has a narrow spectral range. External cavity tuning has been used to tune the QC laser over a small frequency range on the order of a few hundred wavenumbers. But this tuning range is insufficient for most condensed phase spectroscopic applications. This problem can be overcome by the use of a series of QC lasers which may be used sequentially as discrete light sources, or may be combined with beam-combiner dichroic optics in order to result in a highly collimated coherent beam of light with a broad wavelength range of operation. In the latter case, each of the QC lasers may be modulated at a different frequency while still remaining within the frequency bandwidth of the thermopile detector. The intensity information from the individual light sources is easily recovered by analyzing the signal in the Fourier transformed space. In this manner, a multiplex advantage is achieved, further improving the SNR of the measurement.

ATR spectroscopy has also been used in conjunction with microscope optics to obtain the infrared spectrum of small samples or small areas of a large sample. 2-dimensional imaging has also been shown, by adding a focal plane detector imaged into the sample plane. But there is often a need to image the third spatial dimension, that of depth into the sample. An effort in this direction has been accomplished by placing an annular mask in the Fourier plane of the sample as imaged through a microscope objective. By changing the diameter of the annulus, the angle of incidence is changes. But this solution is hindered by a lack of angular resolution, which as stated before often needs to be resolved to a level of a millidegree. The solution to this problem is the use of continuous, precise, variable angle adjustment of the plane of the sample relative to the beam traveling in ATR mode. This mechanism eliminates the need for the microscope objective entirely. The focal plane detector is imaged into the plane of the sample at low magnification and a real time image is formed that can be used to determine and adjust the position of the sample in the beam. The angle of incidence is then varied in order to obtain information about depth variability of the sample. In cases where there is no depth variability, the depth information can be used to improve the quantitative accuracy of the 2-dimensional chemical maps of the sample. In this case, the depth dimension is not imaged, but rather is used to improve the lateral spatial resolution.

One significant difficulty in performing ATR spectroscopy is that the measurement technique is historically very surface sensitive, and therefore very sensitive to the degree of contact obtained between the ATR prism and the sample. Ideally, optical contact should be obtained between the prism and the sample, but this is difficult with real-world samples that might be hard and non-flat. ATR instruments typically include a pressure generating mechanism to press the sample up against the prism. This is not desirable, since it risks breaking the prism. Also, pressure can alter the spectral band positions of the sample. This is therefore a problem that needs to be remedied. By working near to the critical angle, the evanescent wave penetrates much more deeply into the sample, making the technique less surface-sensitive. Now, the sample does not need to be in optical contact with the prism. In fact, it is now possible to perform ATR in a non-contact mode as long as the sample is within a few wavelengths of the prism. Very little pressure needs to be applied to the sample in order to obtain a high quality ATR spectrum. In order to create the deep depth of penetration, a high degree of angular control is needed, in order to operate near the critical angle.

One problem of operating near the critical angle in ATR spectroscopy is that of spectral distortions. Spectral distortions result from the fact that in traditional ATR spectroscopy with a big beam divergence, part of the beam is below the critical angle while another part is above. Also, the refractive index of the sample and prism vary with wavelength, again resulting in distortions. These distortions are a problem that needs to be solved. The solution proposed here is to analyze each wavelength individually. For each wavelength, there exists a clearly defined refractive index for both the sample and the prism. Therefore there is a well defined critical angle at each wavelength. This critical angle can be different for each wavelength in the spectrum. The solution to this problem is to evaluate the plot of absorbance versus angle for each wavelength in the spectrum. It is possible to locate the position of the critical angle from this plot. Then it is a simple matter to move a small angular distance away form this critical angle, to the higher angle side. Repeating this process for each wavelength results in a data array that can be plotted and which represents a true absorption spectrum obtained with greater depth of penetration than before possible. It is also possible to apply an algorithm to automatically produce the deeper depth spectrum. In cases where there is a buried layer in the sample with a unique spectrum, a collection of data at constant and increasing depth with show an interesting phenomenon. For substances with absorption bands that exist at constant concentration through the depth dimension of the sample, the absorbance intensity as a function of angle and depth will be highly ordered and linear. That is, when the depth of penetration is doubled, the absorbance intensity will also be doubled, as the bands obey Beer's Law. But the substances that only exist at deeper depths or exist at different concentrations at deeper depths will be non-linear with respect to Beer's Law. If a linear modeling technique such as Classical Least Squares (CLS) or Multivariate Curve Resolution (MCR) is applied to such a data hypercube, the algorithm will be capable of modeling the linear features but not the non-linear features. The non-linear features will be moved to the error matrix, also known as the spectral residuals matrix. This is significant in that the application of a linear model has resulted in it being possible to identify the non-linear features, which in this case is what we were after. The spectral information about the buried substance exists in the spectral residuals. A good example of a situation like this is the transdermal measurement of blood analytes, for instance glucose. As the evanescent wave enters the skin, and as the angle is moved toward the critical angle, initially there is no glucose or other fluid based spectral information, because the outer skin is dry. The other spectral information related to skin substances is properly modeled by the linear regression technique. The information related to blood analytes will be highly nonlinear with respect to Beer's Law, and so the spectral information from the blood analytes will reside in the spectral residuals. From there it can be accessed and used to build a quantitative model using linear regression.

In one aspect, the present disclosure provides a spectroscopy device for the non-invasive measurement of blood glucose levels. The device measures glucose using the devices and methods described herein. In one embodiment, the skin of a subject is radiated with an electromagnetic radiation beam through the transmitting crystal. A beam is reflected back out and through the crystal. The return beam carries with it information indicating the blood glucose level in the user. The return beam can be analyzed using a suitable processor to provide, for example, a full map of reflected light intensity versus wavelength versus a mapping of the angle of incidence. This information can also be correlated with other biological parameter information either from a patient or from a database. Additionally, the map can be displayed on an LCD and/or communicated to a network. In some embodiments, the spectroscopy device is portable, e.g., a handheld device. In some embodiments, the spectroscopy device is a handheld device. In some embodiments, the functionality is incorporated into a handheld device such as a cell phone. The spectroscopy detector can be built into a smart phone such as an Apple iPhone®, a Palm Pre®, a Blackberry® or the like. Typical handheld cellular phones can also be used. In some embodiments, the measurement is made by the measuring spectroscopy device and sent to another device, e.g., a computer, a server, etc., using wireless communications, e.g., cellular communications, BlueTooth® or WiFi. In some embodiments the measuring spectroscopy device communicates over a hard connection, e.g., through a local area network (LAN), a USB cable or a direct connection to another device (computer, cell phone, etc.). The measuring device itself can also display the measurement information through a device display, e.g., an LCD screen.

III. PR SPECTROSCOPY DEVICES AND COMMUNICATION NETWORKS

As will be appreciated by those skilled in the art, modular and scalable system employing one or more of the spectroscopy devices discussed above can be provided which are comprised of a controller and more than one spectroscopy devices. Controller communicates with each spectroscopy device over a communication media. Communication media may be a wired point-to-point or multi-drop configuration. Examples of wired communication media include Ethernet, USB, and RS-232. Alternatively communication media may be wireless including radio frequency (RF) and optical. The spectroscopy device may have one or more slots for fluid processing devices. Networked devices can be particularly useful in some situations. For example, networked devices that provide blood glucose monitoring results to a care provider (such as a doctor) can facilitate background analysis of compliance of a diabetic with diet, medication and insulin regimes which could then trigger earlier intervention by a healthcare provider when results begin trending in a clinically undesirable direction. Additionally, automatic messages in response to sample measurements can be generated to either the patient monitoring their glucose level and/or to the care provider. In some instances, automatic messages may be generated by the system to either encourage behavior (e.g., a text message or email indicating a patient is on track) or discourage behavior (e.g., a text message or email indicating that sugars are trending upward). Other automated messages could be either email or text messages providing pointers and tips for managing blood sugar. The networked communication system therefore enables background health monitoring and early intervention which can be achieved at a low cost with the least burden to health care practitioners.

Figure 11A:
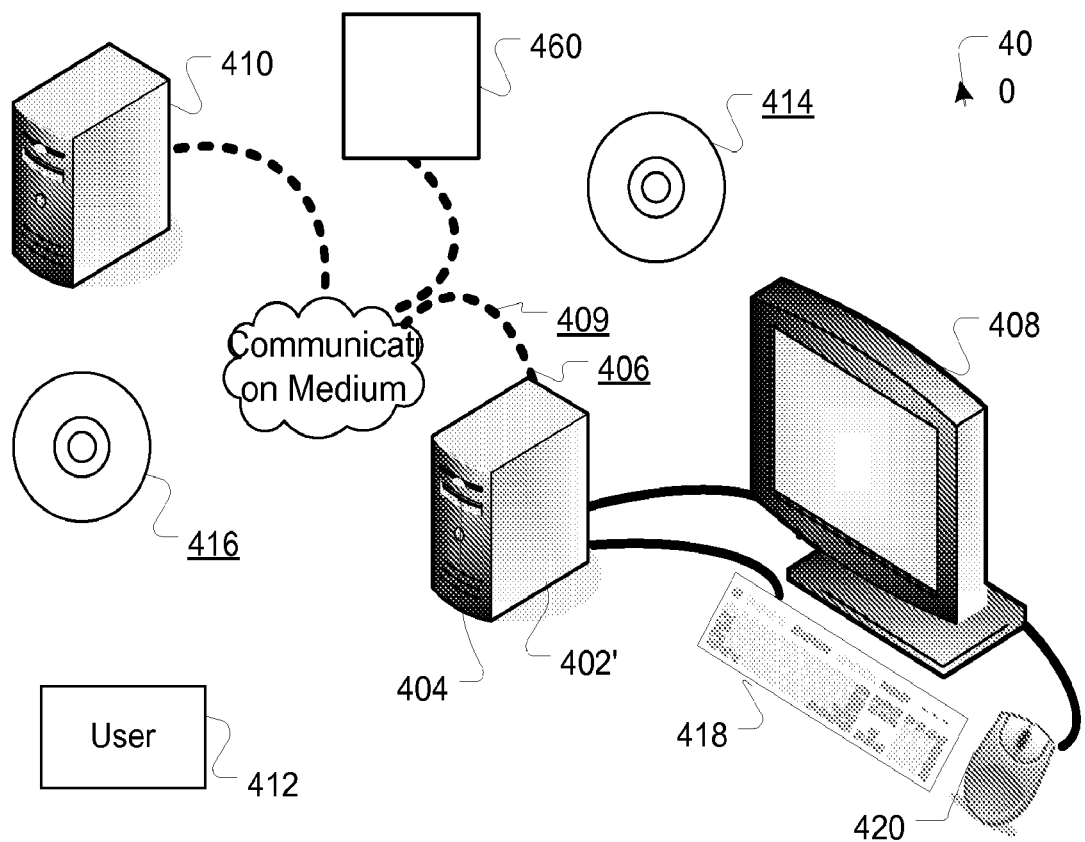
FIG. 11A is a block diagram showing a representative example of a logic device through which a dynamic modular and scalable system can be achieved.

To further appreciate the networked configurations of multiple spectroscopy device in a communication network, FIG. 11A is a block diagram showing a representative example logic device through which a browser can be accessed to control and/or communication with spectroscopy device described above. A computer system (or digital device) 400, which may be understood as a logic apparatus adapted and configured to read instructions from media 414 and/or network port 406, is connectable to a server 410, and has a fixed media 416. The computer system 400 can also be connected to the Internet or an intranet. The system includes central processing unit (CPU) 402, disk drives 404, optional input devices, illustrated as keyboard 418 and/or mouse 420 and optional monitor 408. Data communication can be achieved through, for example, communication medium 409 to a server 410 at a local or a remote location. The communication medium 409 can include any suitable means or mechanism of transmitting and/or receiving data. For example, the communication medium can be a network connection, a wireless connection, or an internet connection. It is envisioned that data relating to the use, operation or function of the one or more spectroscopy device (shown together for purposes of illustration here as 460) can be transmitted over such networks or connections. The computer system can be adapted to communicate with a user (users include healthcare providers, physicians, lab technicians, nurses, nurse practitioners, patients, and any other person or entity which would have access to information generated by the system) and/or a device used by a user. The computer system is adaptable to communicate with other computers over the Internet, or with computers via a server. Moreover the system is configurable to activate one or more devices associated with the network (e.g., diagnostic devices and/or spectroscopy device) and to communicate status and/or results of tests performed by the devices and/or systems.

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can, in a communication network adapted and configured to employ or communicate with one or more spectroscopy devices, be used without departing from the scope of the disclosure. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

The Open System Interconnection (OSI) model was established to standardize transmission between points over the Internet or other networks. The OSI model separates the communications processes between two points in a network into seven stacked layers, with each layer adding its own set of functions. Each device handles a message so that there is a downward flow through each layer at a sending end point and an upward flow through the layers at a receiving end point. The programming and/or hardware that provides the seven layers of function is typically a combination of device operating systems, application software, TCP/IP and/or other transport and network protocols, and other software and hardware.

Typically, the top four layers are used when a message passes from or to a user and the bottom three layers are used when a message passes through a device (e.g., an IP host device). An IP host is any device on the network that is capable of transmitting and receiving IP packets, such as a server, a router or a workstation. Messages destined for some other host are not passed up to the upper layers but are forwarded to the other host. The layers of the OSI model are listed below. Layer 7 (i.e., the application layer) is a layer at which, e.g., communication partners are identified, quality of service is identified, user authentication and privacy are considered, constraints on data syntax are identified, etc. Layer 6 (i.e., the presentation layer) is a layer that, e.g., converts incoming and outgoing data from one presentation format to another, etc. Layer 5 (i.e., the session layer) is a layer that, e.g., sets up, coordinates, and terminates conversations, exchanges and dialogs between the applications, etc. Layer-4 (i.e., the transport layer) is a layer that, e.g., manages end-to-end control and error-checking, etc. Layer-3 (i.e., the network layer) is a layer that, e.g., handles routing and forwarding, etc. Layer-2 (i.e., the data-link layer) is a layer that, e.g., provides synchronization for the physical level, does bit-stuffing and furnishes transmission protocol knowledge and management, etc. The Institute of Electrical and Electronics Engineers (IEEE) sub-divides the data-link layer into two further sub-layers, the MAC (Media Access Control) layer that controls the data transfer to and from the physical layer and the LLC (Logical Link Control) layer that interfaces with the network layer and interprets commands and performs error recovery. Layer 1 (i.e., the physical layer) is a layer that, e.g., conveys the bit stream through the network at the physical level. The IEEE sub-divides the physical layer into the PLCP (Physical Layer Convergence Procedure) sub-layer and the PMD (Physical Medium Dependent) sub-layer.

Wireless networks can incorporate a variety of types of mobile devices, such as, e.g., cellular and wireless telephones, PCs (personal computers), laptop computers, wearable computers, cordless phones, pagers, headsets, printers, PDAs, etc. and suitable for use in a system or communication network that includes one or more spectroscopy devices. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.). Other components can be provided without departing from the scope of the disclosure.

Wireless LANs (WLANs) in which a mobile user can connect to a local area network (LAN) through a wireless connection may be employed for wireless communications between one or more spectroscopy devices. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

In basic IP routing (e.g., outside mobile IP), routing mechanisms rely on the assumptions that each network node always has a constant attachment point to the Internet and that each node's IP address identifies the network link it is attached to. Nodes include a connection point, which can include a redistribution point or an end point for data transmissions, and which can recognize, process and/or forward communications to other nodes. For example, Internet routers can look at an IP address prefix or the like identifying a device's network. Then, at a network level, routers can look at a set of bits identifying a particular subnet. Then, at a subnet level, routers can look at a set of bits identifying a particular device. With typical mobile IP communications, if a user disconnects a mobile device from the Internet and tries to reconnect it at a new subnet, then the device has to be reconfigured with a new IP address, a proper netmask and a default router. Otherwise, routing protocols would not be able to deliver the packets properly.

Figure 11B:
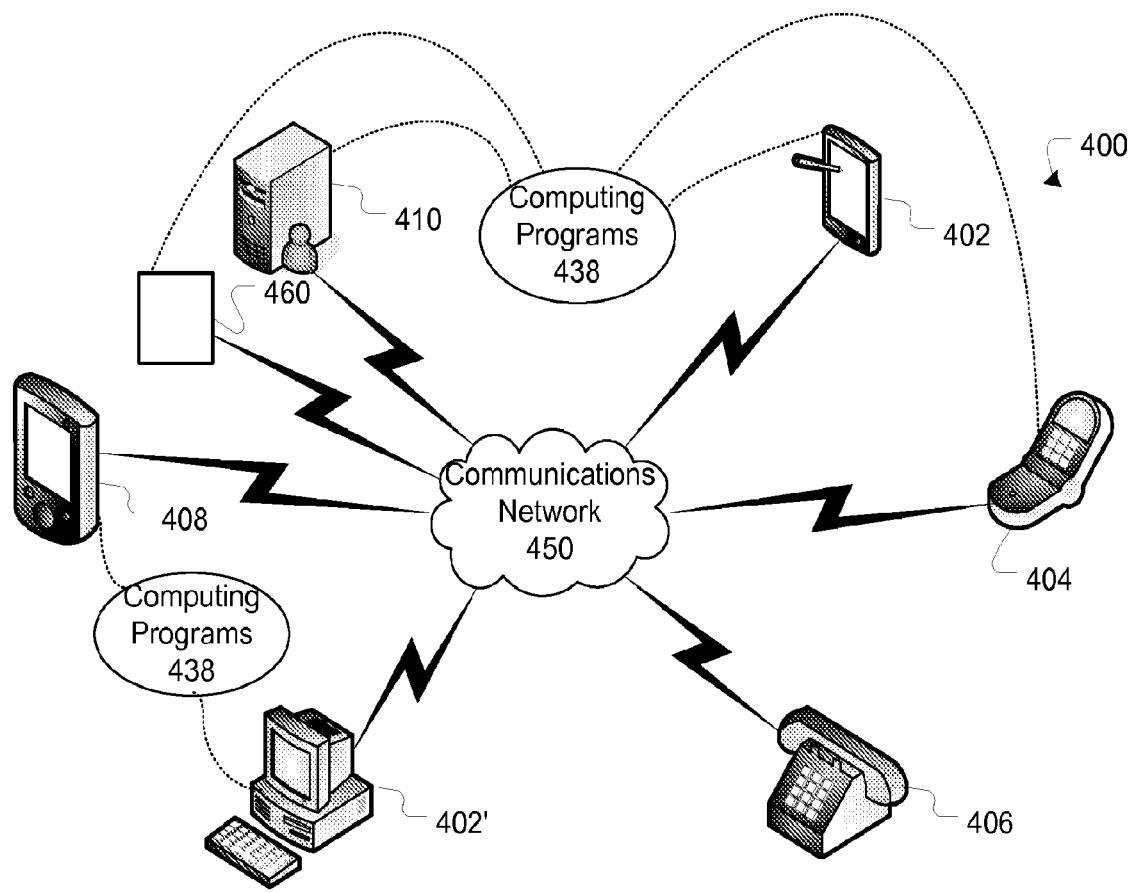
FIG. 11B is a block diagram showing the cooperation of exemplary components of a system suitable for use in a system where dynamic data analysis and modeling is achieved.

Computing system 400, described above, can be deployed as part of a computer network that includes one or devices 460, such as spectroscopy devices disclosed herein. In general, the description for computing environments applies to both server computers and client computers deployed in a network environment. FIG. 11B illustrates an exemplary illustrative networked computing environment 400, with a server in communication with client computers via a communications network 450. As shown in FIG. 11B, server 410 may be interconnected via a communications network 450 (which may be either of, or a combination of a fixed-wire or wireless LAN, WAN, intranet, extranet, peer-to-peer network, virtual private network, the Internet, or other communications network) with a number of client computing environments such as tablet personal computer 402, mobile telephone 404, telephone 406, personal computer 402', and personal digital assistant 408. In a network environment in which the communications network 450 is the Internet, for example, server 410 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the disclosure, including, for example Wireless Markup Language (WML), DoCoMo i-mode (used, for example, in Japan) and XHTML Basic. Additionally, networked computing environment 400 can utilize various data security protocols such as secured socket layer (SSL) or pretty good privacy (PGP). Each client computing environment can be equipped with operating system 438 operable to support one or more computing applications, such as a web browser (not shown), or other graphical user interface (not shown), or a mobile desktop environment (not shown) to gain access to server computing environment 400.

In operation, a user (not shown) may interact with a computing application running on a client computing environment to obtain desired data and/or computing applications. The data and/or computing applications may be stored on server computing environment 400 and communicated to cooperating users through client computing environments over exemplary communications network 450. A participating user may request access to specific data and applications housed in whole or in part on server computing environment 400. These data may be communicated between client computing environments and server computing environments for processing and storage. Server computing environment 400 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

IV. KITS

Bundling all devices, tools, components, materials, and accessories needed to use a spectroscopic device to test a sample into a kit may enhance the usability and convenience of the devices. Suitable kits for detecting the spectral characteristics of a sample, can also include, for example, an electromagnetic radiation source; and a crystal in communication with the electromagnetic radiation source and the sample, the crystal having a high refractive index adapted to reflect the reflect the electromagnetic radiation. The kits can also include other components, including, but not limited to one or more detectors, filters and/or lenses.

V. EXAMPLES

Example 1

Determining Blood Glucose Levels in a Mammal

The devices and methods described above can be uses to detect levels of blood glucose in a mammal. The skin surface of a patient can be placed in proximity to the system. Thereafter, the skin is radiated at a location with an electromagnetic radiation beam through the transmitting crystal. The beam penetrates the skin surface into the blood vessels. A beam is reflected back out from the location within the tissue and through the crystal. The return beam carries with it information indicating the blood glucose level in the user. The return beam can be analyzed using a suitable processor to provide, for example, a full map of reflected light intensity versus wavelength versus a mapping of the angle of incidence. This information can be correlated with other biological parameter information. Additionally, the map can be displayed on an LCD and/or communicated to a network. The device can be configured to use a first wavelength for glucose and a second wavelength at a wavelength where glucose does not absorb. Both angles are rastered through an angular wave, analyzed and a ratio is obtained.

Example 2

Non-Contact Inspection of Materials

Another application is in the area of non-contact inspection. Normally with ATR, it is essential to create a very intimate optical contact between the ATR crystal and the specimen under test. Without this intimate contact, an intermediate layer, usually air, must be considered in the refractive index and depth calculations. With powders and other irregular samples, it is often impossible to remove all of the air space. As a result, the measurement is often unstable from one measurement to the next. The other reason for intimate optical contact is that since the depth of penetration is so small in ATR, the goal is to get the specimen as close to the crystal as possible, where the evanescent field is the strongest. With the present disclosure, it is possible to make the depth of penetration much larger. Therefore we can get very good spectra even when the specimen is not in physical contact with the ATR crystal. The problem of instability in the region of the evanescent field is thereby avoided. An excellent application of this is in the area of non-contact inspection of materials, especially when the material is moving, for instance on a production line. A particular application in the non-contact inspection field would be the examination of pharmaceutical tablets on a production line.

Example 3

Pesticide Detection

Another application is in the area of pesticide detection. A device as substantially described above could be configured to enable consumers to detect levels or types of pesticides on produce in a grocery store, within their pantry or after washing the produce at home.

REFERENCES

J. Fahrenfort, Spectrochim. Acta 17, 698 (1961).
Harrick, N. J., Internal Reflection Spectroscopy, New York: Wiley Interscience, 1967.
Fringeli U P, Goette J, Reiter G, Siam M, and Baurecht D (1998) Structural Investigations of Oriented Membrane Assemblies by FTIR-ATR Spectroscopy. In Proceedings of the 11$^{th}$ International Conference on Fourier Transform Spectroscopy.
Messerschmidt R G, Multiple Internal Reflectance Spectroscopy System, U.S. Pat. No. 4,730,882 (1988).

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus comprising:
   a source of electromagnetic radiation in at least a first wavelength and a second wavelength;
   a crystal having a high refractive index adapted to reflect the electromagnetic radiation in the at least first wavelength and second wavelength;
   a reflector adapted to introduce the electromagnetic radiation in the at least first wavelength and second wavelength to the sample at a location across a range of angles including a critical angle between the crystal and the sample;
   a detector for detecting a return electromagnetic radiation from each of the at least first wavelength and second wavelength from the sample.

2. The apparatus of claim 1 further comprising a housing adapted to contain the electromagnetic radiation source, crystal, reflector and detector.

3. The apparatus of claim 1 wherein the detector is a single element detector.

4. The apparatus of claim 1 wherein the detector is a single element mercury cadmium telluride detector.

5. The apparatus of claim 1 wherein the detector is a linear array detector.

6. The apparatus of claim 1 wherein the detector is a 2-dimensional array detector.

7. The apparatus of claim 1 wherein the electromagnetic radiation source is adapted to deliver an electromagnetic radiation to the sample at an angle of incidence below the critical angle.

8. The apparatus of claim 7 wherein the electromagnetic radiation source is further adapted to adjust an electromagnetic radiation delivered to the sample to approach and pass the critical angle.

9. The apparatus of claim 1 wherein the electromagnetic radiation source is adapted to deliver an electromagnetic radiation to the sample at an angle of incidence above the critical angle.

10. The apparatus of claim 9 wherein the electromagnetic radiation source is further adapted to adjust and electromagnetic radiation delivered to the sample to approach and pass the critical angle.

11. The apparatus of claim 1 further comprising a data processor in communication with the detector.

12. The apparatus of claim 11 wherein the data processor is further adapted to generate a critical angle map of the sample from one or more electromagnetic radiation detections received by the detector from the sample.

13. The apparatus of claim 1 wherein the electromagnetic radiation source is a quantum cascade laser.

14. The apparatus of claim 1 wherein the electromagnetic radiation is collimated.

15. The apparatus of claim 1 wherein the apparatus is less than 1 cubic foot in volume.

16. The apparatus of claim 1 wherein the apparatus is less than 125 cubic inches in volume.

17. The apparatus of claim 1 wherein the apparatus is handheld.

18. The apparatus of claim 1 wherein the apparatus is less than 8 cubic inches in volume.

19. The apparatus of claim 12 further comprising a display screen adapted and configured to display the critical angle map.

20. The apparatus of claim 11 wherein the data processor is adapted to generate a full map of reflected light intensity versus wavelength versus a mapping of the angle of incidence from the detected electromagnetic radiation.

21. The apparatus of claim 1 further comprising a drive mechanism adapted to pivot the crystal about an axis.

22. The apparatus of claim 1 further comprising a cooler adapted to cool the detector.

23. The apparatus of claim 1 further comprising a filter.

24. The apparatus of claim 1 further comprising a lens configured to image the electromagnetic radiation onto a detector area less than 1 mm$^2$.

25. A method for detecting the spectral characteristics of a sample comprising:
placing a sample in proximity to a crystal;
emitting an electromagnetic radiation from an electromagnetic radiation source in at least a first wavelength and a second wavelength through the crystal at a fixed or variable angle of incidence;
introducing the electromagnetic radiation in the at least first wavelength and second wavelength to the sample at a location through the crystal at an angle of incidence including a critical angle between the crystal and the sample; and
detecting a return electromagnetic radiation from the at least first wavelength and second wavelength from the sample.

26. The method of claim 25 further comprising the steps of introducing the electromagnetic radiation at an angle of incidence below the critical angle; and
increasing the angle of incidence of the electromagnetic radiation incrementally whereby the angle of incidence approaches and passes the critical angle.

27. The method of claim 26 further comprising the steps of introducing the electromagnetic radiation at an angle of incidence above the critical angle; and
decreasing the angle of incidence of the electromagnetic radiation incrementally whereby the angle of incidence approaches and passes the critical angle.

28. The method of claim 26 further comprising the step of generating a full map of reflected light intensity versus wavelength versus a mapping of the angle of incidence.

29. The method of claim 28 further comprising the step of displaying a generated map.

30. The method of claim 26 further comprising the step of comparing the detected electromagnetic radiation to a database of critical angle measurements.

31. The method of claim 30 further comprising the step of displaying a detected electromagnetic radiation parameter and one or more critical angle measurements from the database.

32. The method of claim 25 further comprising the step of filtering the electromagnetic radiation.

33. The method of claim 25 further comprising the step of pivoting the crystal about an axis.

34. The method of claim 25 further comprising the step of cooling the detector.

35. The method of claim 25 further comprising the step of imaging the electromagnetic radiation onto a detector area less than 1 mm$^2$.

36. A networked apparatus comprising:
a memory;
a processor;
a communicator;
a display; and
an apparatus for detecting spectral characteristic comprising a source of electromagnetic radiation in at least a first wavelength and a second wavelength; a crystal having a high refractive index adapted to reflect the electromagnetic radiation from the at least first wavelength and second wavelength; a reflector adapted to introduce the electromagnetic radiation in the at least first wavelength and second wavelength to the sample at a location across a range of angles including a critical angle between the crystal and the sample; and a detector for detecting a return electromagnetic radiation from each of the at least first wavelength and second wavelength from the electromagnetic radiation from the sample.

37. A communication system, comprising:
an apparatus for detecting spectral characteristic comprising a source of electromagnetic radiation in at least a first wavelength and a second wavelength; a crystal having a high refractive index adapted to reflect the electromagnetic radiation from the at least first wavelength and second wavelength; a reflector adapted to introduce the electromagnetic radiation in the at least first wavelength and second wavelength to the sample at a location across a range of angles including a critical angle between the crystal and the sample; and a detector for detecting a return electromagnetic radiation from each of the at least first wavelength and second wavelength from the electromagnetic radiation from the sample;
a server computer system;
a measurement module on the server computer system for permitting the transmission of a measurement from a system for detecting spectral characteristics over a network;

at least one of an API engine connected to at least one of the system for detecting spectral characteristics and the device for detecting spectral characteristics to create an message about the measurement and transmit the message over an API integrated network to a recipient having a predetermined recipient user name, an SMS engine connected to at least one of the system for detecting spectral characteristics and the device for detecting spectral characteristics to create an SMS message about the measurement and transmit the SMS message over a network to a recipient device having a predetermined measurement recipient telephone number, and an email engine connected to at least one of the system for detecting spectral characteristics and the device for detecting spectral characteristics to create an email message about the measurement and transmit the email message over the network to a recipient email having a predetermined recipient email address.

38. The communication system of claim 37, further comprising a storing module on the server computer system for storing the measurement on the system for detecting spectral characteristics server database.

39. The communications system of claim 38, wherein at least one of the system for detecting spectral characteristics and the device for detecting spectral characteristics is connectable to the server computer system over at least one of a mobile phone network and an Internet network, and a browser on the measurement recipient electronic device is used to retrieve an interface on the server computer system.

40. The communications system of claim 38, wherein a plurality of email addresses are held in a system for detecting spectral characteristics database and fewer than all the email addresses are individually selectable from the diagnostic host computer system, the email message being transmitted to at least one recipient email having at least one selected email address.

41. The communications system of claim 40, wherein at least one of the system for detecting spectral characteristics and the device for detecting spectral characteristics is connectable to the server computer system over the Internet, and a browser on the measurement recipient electronic device is used to retrieve an interface on the server computer system.

42. The communications system of claim 39, wherein a plurality of user names are held in the system for detecting spectral characteristics database and fewer than all the user names are individually selectable from the diagnostic host computer system, the message being transmitted to at least one measurement recipient user name via an API.

43. The communications system of claim 42, wherein the measurement recipient electronic device is connectable to the server computer system over the Internet, and a browser on the measurement recipient electronic device is used to retrieve an interface on the server computer system.

44. The communications system of claim 39, wherein the measurement recipient electronic device is connected to the server computer system over a cellular phone network.

45. The communications system of claim 44, wherein the measurement recipient electronic device is a mobile device.

46. The communications system of claim 45, further comprising: an interface on the server computer system, the interface being retrievable by an application on the mobile device.

47. The communications system of claim 45, wherein the SMS measurement is received by a message application on the mobile device.

48. The communications system of claim 47, wherein a plurality of SMS measurements are received for the measurement, each by a respective message application on a respective recipient mobile device.

49. The communications system of claim 39, wherein the at least one SMS engine receives an SMS response over the cellular phone SMS network from the mobile device and stores an SMS response on the server computer system.

50. The communications system of claim 49, wherein a measurement recipient phone number ID is transmitted with the SMS measurement to the SMS engine and is used by the server computer system to associate the SMS measurement with the SMS response.

51. The communications system of claim 39, wherein the server computer system is connectable over a cellular phone network to receive a response from the measurement recipient mobile device.

52. The communications system of claim 51, wherein the SMS measurement includes a URL that is selectable at the measurement recipient mobile device to respond from the measurement recipient mobile device to the server computer system, the server computer system utilizing the URL to associate the response with the SMS measurement.

53. The communications system of claim 39, further comprising:
a downloadable application residing on the measurement recipient mobile device, the downloadable application transmitting the response and a measurement recipient phone number ID over the cellular phone network to the server computer system, the server computer system utilizing the measurement recipient phone number ID to associate the response with the SMS measurement.

54. The communications system of claim 39, further comprising:
a transmissions module that transmits the measurement over a network other than the cellular phone SMS network to a measurement recipient user computer system, in parallel with the measurement that is sent over the cellular phone SMS network.

55. The communication system of claim 39 further comprising
a downloadable application residing on the measurement recipient host computer, the downloadable application transmitting a response and a measurement recipient phone number ID over the cellular phone network to the server computer system, the server computer system utilizing the measurement recipient phone number ID to associate the response with the SMS measurement.

56. A networked apparatus comprising:
a memory;
a processor;
a communicator;
a display; and
an apparatus for detecting the spectral characteristics of a sample comprising an electromagnetic radiation source adapted to excite a sample with electromagnetic radiation, a crystal in communication with the electromagnetic radiation source and the sample, the crystal having a high refractive index adapted to reflect the electromagnetic radiation, a reflector adapted to introduce the electromagnetic radiation to the sample at a location at an angle of incidence including a critical angle between the crystal and the sample, and a detector for detecting an electromagnetic radiation from the sample.

57. A communication system, comprising:
an apparatus for detecting the spectral characteristics of a sample comprising an electromagnetic radiation source adapted to excite a sample with electromagnetic radiation, a crystal in communication with the electromagnetic radiation source and the sample, the crystal having a high refractive index adapted to reflect the electromagnetic radiation, a reflector adapted to introduce the electromagnetic radiation to the sample at a location at an angle of incidence including a critical angle between the crystal and the sample, and a detector for detecting an electromagnetic radiation from the sample;

a server computer system;

a measurement module on the server computer system for permitting the transmission of a measurement from a system for detecting spectral characteristics over a network;

at least one of an API engine connected to at least one of the system for detecting spectral characteristics and the device for detecting spectral characteristics to create an message about the measurement and transmit the message over an API integrated network to a recipient having a predetermined recipient user name, an SMS engine connected to at least one of the system for detecting spectral characteristics and the device for detecting spectral characteristics to create an SMS message about the measurement and transmit the SMS message over a network to a recipient device having a predetermined measurement recipient telephone number, and an email engine connected to at least one of the system for detecting spectral characteristics and the device for detecting spectral characteristics to create an email message about the measurement and transmit the email message over the network to a recipient email having a predetermined recipient email address.

58. The communication system of claim 57, further comprising a storing module on the server computer system for storing the measurement on the system for detecting spectral characteristics server database.

59. The communications system of claim 58, wherein at least one of the system for detecting spectral characteristics and the device for detecting spectral characteristics is connectable to the server computer system over at least one of a mobile phone network and an Internet network, and a browser on the measurement recipient electronic device is used to retrieve an interface on the server computer system.

60. The communications system of claim 58, wherein a plurality of email addresses are held in a system for detecting spectral characteristics database and fewer than all the email addresses are individually selectable from the diagnostic host computer system, the email message being transmitted to at least one recipient email having at least one selected email address.

61. The communications system of claim 60, wherein at least one of the system for detecting spectral characteristics and the device for detecting spectral characteristics is connectable to the server computer system over the Internet, and a browser on the measurement recipient electronic device is used to retrieve an interface on the server computer system.

62. The communications system of claim 59, wherein a plurality of user names are held in the system for detecting spectral characteristics database and fewer than all the user names are individually selectable from the diagnostic host computer system, the message being transmitted to at least one measurement recipient user name via an API.

63. The communications system of claim 62, wherein the measurement recipient electronic device is connectable to the server computer system over the Internet, and a browser on the measurement recipient electronic device is used to retrieve an interface on the server computer system.

64. The communications system of claim 62, wherein the measurement recipient electronic device is connected to the server computer system over a cellular phone network.

65. The communications system of claim 64, wherein the measurement recipient electronic device is a mobile device.

66. The communications system of claim 65, further comprising: an interface on the server computer system, the interface being retrievable by an application on the mobile device.

67. The communications system of claim 65, wherein the SMS measurement is received by a message application on the mobile device.

68. The communications system of claim 67, wherein a plurality of SMS measurements are received for the measurement, each by a respective message application on a respective recipient mobile device.

69. The communications system of claim 59, wherein the at least one SMS engine receives an SMS response over the cellular phone SMS network from the mobile device and stores an SMS response on the server computer system.

70. The communications system of claim 69, wherein a measurement recipient phone number ID is transmitted with the SMS measurement to the SMS engine and is used by the server computer system to associate the SMS measurement with the SMS response.

71. The communications system of claim 59, wherein the server computer system is connectable over a cellular phone network to receive a response from the measurement recipient mobile device.

72. The communications system of claim 53, wherein the SMS measurement includes a URL that is selectable at the measurement recipient mobile device to respond from the measurement recipient mobile device to the server computer system, the server computer system utilizing the URL to associate the response with the SMS measurement.

73. The communications system of claim 59, further comprising:

a downloadable application residing on the measurement recipient mobile device, the downloadable application transmitting the response and a measurement recipient phone number ID over the cellular phone network to the server computer system, the server computer system utilizing the measurement recipient phone number ID to associate the response with the SMS measurement.

74. The communications system of claim 59, further comprising:

a transmissions module that transmits the measurement over a network other than the cellular phone SMS network to a measurement recipient user computer system, in parallel with the measurement that is sent over the cellular phone SMS network.

75. The communication system of claim 59 further comprising a downloadable application residing on the measurement recipient host computer, the downloadable application transmitting a response and a measurement recipient phone number ID over the cellular phone network to the server computer system, the server computer system utilizing the measurement recipient phone number ID to associate the response with the SMS measurement.

* * * * *

UNITED STATES PATENT AND TRADEMARK OFFICE
CERTIFICATE OF CORRECTION

PATENT NO.           : 9,041,923 B2                                Page 1 of 1
APPLICATION NO.      : 13/263386
DATED                : May 26, 2015
INVENTOR(S)          : Robert G. Messerchmidt It is certified that error appears in the above-identified patent and that said Letters Patent is hereby corrected as shown below:

On the Title Page, Item (56)

On page 3, in column 1, under "Other Publications", line 61, delete "Applicaton" and insert --Application--, therefor On page 3, in column 2, under "Other Publications", line 2, delete "Aciton" and insert --Action--, therefor On page 4, in column 2, under "Other Publications", line 19, delete "201080025328,9," and insert --201080025328.9,--, therefor Signed and Sealed this
Third Day of November, 2015

Michelle K. Lee
*Director of the United States Patent and Trademark Office*